(12) United States Patent
McArthur

(10) Patent No.: US 9,550,991 B2
(45) Date of Patent: Jan. 24, 2017

(54) TRANSCRIPTION FACTOR DECOYS

(75) Inventor: Michael McArthur, Norwich (GB)

(73) Assignee: PROCARTA BIOSYSTEMS LTD., Norwich (GB)

( * ) Notice: Subject to any disclaimer, the term of this patent is extended or adjusted under 35 U.S.C. 154(b) by 0 days.

(21) Appl. No.: 13/638,764

(22) PCT Filed: Mar. 30, 2011

(86) PCT No.: PCT/GB2011/050657
§ 371 (c)(1),
(2), (4) Date: Dec. 16, 2012

(87) PCT Pub. No.: WO2011/121357
PCT Pub. Date: Oct. 6, 2011

(65) Prior Publication Data
US 2013/0252881 A1    Sep. 26, 2013

Related U.S. Application Data

(60) Provisional application No. 61/320,195, filed on Apr. 1, 2010.

(30) Foreign Application Priority Data

Apr. 1, 2010  (GB) .................................. 1005545.7

(51) Int. Cl.
*A01N 37/18* (2006.01)
*C12N 15/113* (2010.01)
*A61K 31/7088* (2006.01)

(52) U.S. Cl.
CPC ......... *C12N 15/113* (2013.01); *A61K 31/7088* (2013.01); *C12N 2310/13* (2013.01)

(58) Field of Classification Search
CPC .............. C12N 15/113; C12N 2310/13; A61K 31/7088

See application file for complete search history.

(56) References Cited

U.S. PATENT DOCUMENTS

| 5,977,084 A | 11/1999 | Szoka, Jr. et al. |
| 6,090,619 A * | 7/2000 | Weissig ................. C12N 15/87 435/320.1 |
| 6,133,026 A | 10/2000 | Huang et al. |

(Continued)

FOREIGN PATENT DOCUMENTS

| EP | 2266626 | 12/2010 |
| WO | WO 93/19768 | 10/1993 |

(Continued)

OTHER PUBLICATIONS

Leang Ching et al: "Genome-wide analysis of the RpoN regulon in Geobacter sulfurreducens", BMC Genomics, Biomed Central, London, GB, vol. 10, No. 1, Jul. 22, 2009 (Jul. 22, 2009), p. 331, XP021056141.*

(Continued)

*Primary Examiner* — Reza Ghafoorian
(74) *Attorney, Agent, or Firm* — Knobbe, Martens, Olson & Bear, LLP

(57) ABSTRACT

Decoy nucleic acid sequences comprising a sequence encoding all or part of a binding site for bacterial sigN alternative sigma54 factor are described. Uses of the decoys in antibacterial complexes and for the treatment of bacterial infections are also described.

37 Claims, 6 Drawing Sheets

(56) References Cited

U.S. PATENT DOCUMENTS

Figure 2:
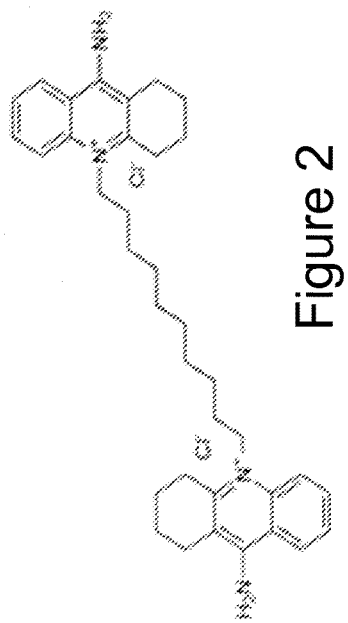

| | | |
|---|---|---|
| 6,551,795 B1 | 4/2003 | Rubenfield |
| 9,024,005 B2 | 5/2015 | McArthur |
| 2004/0014956 A1 | 1/2004 | Woolf et al. |
| 2005/0227257 A1 | 10/2005 | Abravaya et al. |
| 2007/0011759 A1 | 1/2007 | Khan |
| 2007/0014840 A1 | 1/2007 | Lee et al. |
| 2007/0031850 A1 | 2/2007 | Mounts et al. |
| 2007/0104775 A1 | 5/2007 | Panzner et al. |
| 2009/0099108 A1 | 4/2009 | Jones |
| 2011/0009476 A1 | 1/2011 | McArthur |
| 2011/0251264 A1 | 10/2011 | McArthur et al. |
| 2014/0080190 A1 | 3/2014 | Atkinson et al. |
| 2014/0274800 A1 | 9/2014 | McArthur |
| 2015/0196652 A1 | 7/2015 | McArthur |

FOREIGN PATENT DOCUMENTS

| | | | |
|---|---|---|---|
| WO | WO 94/23699 | 10/1994 | |
| WO | WO 95/34647 | 12/1995 | |
| WO | WO 97/30070 A1 | 8/1997 | |
| WO | WO 99/13096 A1 | 3/1999 | |
| WO | WO 01/75067 | 11/2001 | |
| WO | WO 2004/016754 | 2/2004 | |
| WO | WO 2004/030699 A1 | 4/2004 | |
| WO | WO 2004/067709 A2 | 8/2004 | |
| WO | WO 2005/062854 | 7/2005 | |
| WO | WO 2006/096140 | 9/2006 | |
| WO | WO 2007/013480 | 2/2007 | |
| WO | WO 2007/137301 | 11/2007 | |
| WO | WO 2008/024389 | 2/2008 | |
| WO | WO 2008/092142 | 7/2008 | |
| WO | WO2009044154 A2 * | 4/2009 | ............... C12Q 1/68 |
| WO | WO 2009/044154 A2 | 9/2009 | |
| WO | WO 2010/038083 | 4/2010 | |
| WO | WO 2011/098829 A1 | 8/2011 | |

OTHER PUBLICATIONS

Barrios et al: "Compilation and analysis of sigma(54)-dependent promoter sequences", Nucleic Acids Research, vol. 27, No. 22, Nov. 15, 1999 (Nov. 15, 1999), pp. 4305-4313, XP55001633.*

M.J. Mann: "Transcription Factor Decoys: A New Model for Disease Intervention", Annals of the New York Academy of Sciences, vol. 1058, No. 1, Nov. 1, 2005 (Nov. 1, 2005 ), pp. 128-139, XP55001514.*

Siddhesh et al., DNA-based Therapeutics and DNA Delivery Systems: a Comprehensive Review, The AAPS Journal 2005:7 (1) Article 9.*

Buck et al., The Bacterial Enhancer-Dependent ς 54(ς N) Transcription Factor, J. Bacteriol. Aug. 2000 vol. 182 No. 15 4129-4136.*

Coleman et al., Chapter 12, The Role of Sigma Factors in Regulating Bacterial Stress Responses and Pathogenesis, in Molecular Paradigms of Infectious Disease, A Bacterial Perspective, Nickerson & Schurr, Eds., Springer, 2006.*

Mann & Dzau, Therapeutic applications of transcription factor decoy oligonucleotides, The Journal of Clinical Investigation, Nov. 2000, vol. 106, No. 9, pp. 1071-1075.*

Barrios et al., Compilation and analysis of σ54-dependent promoter sequences, Nucleic Acids Research, 1999, vol. 27, No. 22, pp. 4305-4313.*

Lee et al., Advantages of the Circular Dumbbell Decoy in Gene Therapy and Studies of Gene Regulation, Current Drug Targets, 2003, 4, 619-623.*

Coles et al., Trial of Dequalinium for Skin Infections, British Medical Jl., Oct. 25, 1958, pp. 1014-1017.*

Gutierrez-Lugo et al., Dequalinium, a New Inhibitor of *Mycobacterium tuberculosis* Mycothiol Ligase Identified by High-Throughput Screening, Jl. of Molecular Screening, 2009 14:643 (original online publication date Jun. 12, 2009).*

Weissig et al.(2006) J. Liposome Research 16:249-264.*

Oren and Shai, Mode of Linear Amphipathic α-Helical Antimicrobial Peptides, Biopolymers (Peptide Science) vol. 47, 451-463 (1998).*

Galanakis, J. Med. Chem. 1995, 38, 3536-3546 (Galanakis).*

Patil et al., DNA-based Therapeutics and DNA Delivery Systems: A Comprehensive Review, The AAPS Jl. 2005; 7(1) Article 9, E61-E77.*

Weissig et al., DNA binding cationic bolasomes with delocalized charge center A structure-activity relationship study, S.T.P. Pharma Sciences, 11(1)91-96 2001 (Weissig2).*

Leang at al "Genome wide analysis of the RpoN regulon . . . " BMC Genomics, Biomed Central, London vol. 10, No. 1, Jul. 22, 2009.

Barrios et al. "Compilation and analysis of sigma(54) dependent promoter sequences" Nucleic Acid Research, vol. 27, No. 22, Nov. 15, 1999.

Mann et al. "Transcription factor decoys: A new model for disease intervention" Ann NY Accad Sci. vol. 1058 No. 1, Nov. 1, 2005.

Abe et al "Contribution of Asian mouse subspecies *Mus musculus molossinus* to genomic constitution . . . " Gene Research vol. 14 No. 12 Jan. 1, 2004. EMBL database Accession No. EMBL AG504103 Jun. 4, 2004. *Mus musculus molossinus* DNA clone MSMg01-405L22.T7 genomic survey sequence.

McArthur et al. "Manipulating and understanding antibiotic production . . . " PNAS vol. 105 No. 3 Jan. 11, 2003.

Arthur et al., "Regulated interactions between partner and non-partner sensors and response regulators that control glycopeptide resistance gene expression in enterococci," Microbiology, vol. 145, pp. 1849-1858 (1999).

Boyd et al., "VanG-Type Vancomycin-Resistant Enterococcus faecilis Strains Isolated in Canada," Antimicrobial Agents and Chemotherapy, Jun. 2006, vol. 50(6), pp. 2217-2221.

Buck et al. Nature. vol. 358, Jul. 30, 1992, p. 422-424.

Chang et al., "Conformational Changes in DNA upon Ligand Binding Monitored by Circular Dichroism," *Int. J. Mol. Sci.*, vol. 13, pp. 3394-3413 (2012).

Choi et al., "Increasing vancomycin susceptibility in vancomycin resistant enterococci by vanH promoter and ddl transformation," Journal of Infection, vol. 48, pp. 314-319 (2004).

Cranenburgh et al., "*Escherichia coli* strains that allow antibiotic-free plasmid selection and maintenance by repressor titration," Nucleic Acids Research, 2001, vol. 29, No. 5 e26, Oxford University Press, XP-002514866.

Dapa et al., "Multiple Factors Modulate Biofilm Formation by the Anaerobic Pathogen Clostridium difficile," Journal of Bacteriology, vol. 195(3), pp. 545-555 (Feb. 2013), with additional data from online version.

Dawson et al., "Characterisation of Clostridium difficile Biofilm Formation, a Role for Spo0A," PLOS One, vol. 7(12), pp. 1-13 (Dec. 2012), with additional data from online version.

Deakin et al., "The Clostridium difficile spo0A Gene Is a Persistence and Transmission Factor," Infection and Immunity, vol. 80(8), pp. 2704-2711 (Aug. 2012), with additional data from online version.

D'Souza et al., "DQAsome-mediated delivery of plasmid DNA toward mitochondria in living cells," Journal of Controlled Release, vol. 92, pp. 189-197 (2003).

Fuhrhop et al., "Bolaamphiphiles," *Chem. Rev.*, vol. 104, pp. 2901-2937 (2004).

Gross et al., Bacterial Sigma Factors, Chapter 6, pp. 129-176, Cold Spring Harbor, 1992.

Heyes et al, "Antitumor Evaluation of a Ribonuclease Resistant Double-Stranded RNA-Polyquaternary Ammonium Complex (BRL 10739)," European J. of Cancer, 1965, Permagon, vol. 10, No. 7, Jul. 1, 1974. Abstract, p. 431, col. 2 para 2, ph 432 col. 1 Para 1, fig 1.

Hugo et al., "Mode of Action of the Antibacterial Compound Dequalinium Acetate," *Applied Microbiology*, vol. 17(1), pp. 118-127 (Jan. 1969).

International Search Report and Written Opinion of the International Searching Authority for PCT/GB2014/050752, mailed on Jun. 16, 2014.

(56) References Cited

OTHER PUBLICATIONS

Kypr et al., "Circular dichroism and conformational polymorphism of DNA," *Nucleic Acids Research*, vol. 37(6), pp. 1713-1725 (2009).
Legendre et al, "Biochemical, Morphological and Functional Analyses of a Cyclic Peptide, Phospholipid, and DNA Ternary Complex Used for Gene Delivery," J. Liposome Res., vol. 8(3), pp. 347-366, Aug. 1, 1998.
Lim et al., "Sequence-independent inhibition of RNA transcription by DNA dumbbells and other decoys," Nucleic Acids Research, 1997, pp. 575-581, vol. 25, No. 3, XP002522068.
Moellering Jr., "Discovering new antimicrobial agents," *International Journal of Antimicrobial Agents*, vol. 37, pp. 2-9 (2011).
Morishita et al., "Application of Transcription Factor "Decoy" Strategy as Means of Gene Therapy," Circulation Research, 1998, vol. 82, pp. 1023-1028.
Norris et al., "Prokaryotic gene therapy to combat multidrug resistant bacterial infection," Gene Therapy, 2000, 723-725, vol. 7, XP009004366.
Onizuka et al., "CO2 response for expression of ribulose-1,5-bisphosphate carboxylase/oxygenase genes is inhibited by AT-rich decoy in the cyanobacterium," FEBS Letters, FEBS 27178, 2003, pp. 42-46, vol. 542.
Parker et al, "Methodologies for Monitoring Nanoparticle Formation by Self-Assembly of DNA with Poly(L-lysine)," Analytical Biochem., Academic Press Inc., NY, vol. 302, No. 1, Mar. 1, 2002, pp. 75-80, abstract, p. 76, col. 1, para 2.
Quagliotto et al., "Gemini Pyridinium Surfactants: Synthesis and Conductometric Study of a Novel Class of Amphiphiles," *J. Org. Chem.*, vol. 68(20), pp. 7651-7660 (2003).
Quagliotto et al., "Synthesis and Characterization of Highly Fluorinated Gemini Pyridinium Surfactants," *Eur. J. Org. Chem.*, pp. 3167-3177 (2009).
Rosenbusch et al., "C. difficile 630Δerm Spo0A Regulates Sporulation, but Does Not Contribute to Toxin Production, by Direct High-Affinity Binding to Target DNA," PLOS One, vol. 7(10), pp. 1-12 (Oct. 2012), with additional data from online version.
Saujet et al., "The Key Sigma Factor of Transition Phase, SigH, Controls Sporulation, Metabolism, and Virulence Factor Expression in Clostridium difficile," Journal of Bacteriology, vol. 193(13), pp. 3186-3196 (Jul. 2011), with additional data from online version.
Sebaihia et al., "The multidrug-resistant human pathogen Clostridium difficile has a highly mobile, mosaic genome," Nature Genetics, vol. 18(7), pp. 779-786 (Jul. 2006), with additional data from online version.
Sharma et al., "Heterocyclic Cationic Gemini Surfactants: A Comparative Overview of Their Synthesis, Self-assembling, Physicochemical, and Biological Properties," *Medicinal Research Reviews*, vol. 34(1), pp. 1-44 (2014).
Shiraishi et al., "Targeted Delivery of Plasmid DNA into the Nucleus of Cells via Nuclear Localization Signal Peptide Conjugated to DNA Intercalating Bis- and Trisacridines," Bioconjugate Chem., vol. 16, pp. 1112-1116 (2005).
Stabler et al., "Comparative genome and phenotypic analysis of Clostridium difficile 027 strains provides insight into the evolution of a hypervirulent bacterium," Genome Biology, vol. 10(9), pp. R102-R102.15 (2009), with additional data from online version.
Theuretzbacher, "Accelerating resistance, inadequate antibacterial drug pipelines and international Responses," *International Journal of Antimicrobial Agents*, vol. 39, pp. 295-299 (2012).
Toledano et al., "Redox-Dependent Shift of OxyR-DNA Contacts along an Extended DNA-Binding Site: A Mechanism for Differential Promoter Selection," Cell, Sep. 9, 1994, pp. 897-909, vol. 78, XP024246465.
Torres Viera et al., "Restoration of Vancomycin Susceptibility in Enterococcus faecalis by Antiresistance Determinant Gene Transfer," Antimicrobial Agents and Chemotherapy, vol. 45(3), pp. 973-975 (Mar. 2001).
Underwood et al., "Characterization of the Sporulation Initiation Pathway of Clostridium difficile and Its Role in Toxin Production," Journal of Bacteriology, vol. 191(23), pp. 7296-7305 (Dec. 2009), with additional data from online version.
Weissig et al., "DQAsomes: A Novel Potential Drug and Gene Delivery System Made from Dequalinium™," Pharmaceutical Res., vol. 15(2), pp. 334-337 (1998).
Weissig et al., "Selective DNA Release from DQAsome/DNA Complexes at Mitochondria-Like Membranes," *Drug Delivery*, vol. 7, pp. 1-5 (2000).
Weissig et al., "Cationic bolasomes with delocalized charge centers as mitochondria-specific DNA delivery systems," Advanced Drug Delivery Reviews, vol. 49, pp. 127-149 (2001).
Zhang et al., "The hydrolysis of cationic polycarboxybetaine esters to zwitterionic polycarboxybetaines with controlled properties," J. Biomaterials, 2008, vol. 29, No. 36, Dec. 2008. Abstract, p. 4720, col. 2, para 5, para 6, structure 1, table 1.
Endoh et al. (Molecular Microbiology, vol. 55, issue 3 pp. 897-911, 2005).
Prouty et al. Molecular Microbiology (2001) 39(6), 1595-1609.
Zubkov et al., "Synthesis and Antimicrobial Activity of 3-Aminomethyl-Substituted Quinolones," UDC 54.057:547.831.7/8:615.28 (2003).
Chen et al. Nucleic Acids Research, 2007, 35:6762-6777.
Chen et al. Nucleic Acids Research, 2007, 35:6762-6777 (supplementary material).
Maki et al., Antimicrobial Agents Chemother., (2004) 48:1953.
Ow et al. PNAS 80:2524-2528, 1983.
Jefferson et al., "The teicoplanin-associated locus regulator (TcaR) and the intercellular adhesion locus regulator (IcaR) are transcriptional inhibitors of the ica locus in *Staphylococcus aureus*," J. Bacteriol, vol. 186(8), pp. 2449-2456 (Apr. 2004).
Liu et al., Clinical Practice Guidelines by the Infectious Diseases Society of America for the Treatment of Methicillin-Resistant *Staphylococcus aureus* Infections in Adults and Children, Clin. Infect. Diseases Advance, CID 2011 :52, 1-38, Jan. 4, 2011.
Viera et al., Restoration of Vancomycin Susceptibility in Enterococcus faecilis by Antiresistance Determinant Gene Transfer, Antimicrobial Agents and Chemotherapy, Mar. 2001, p. 973-975.
Morris et al., "DNA Distortion and Nucleation of Local DNA Unwinding within Sigma-54 (σN) Holoenzyme Closed Promoter Complexes," The Journal of Biological Chemistry, vol. 269(15), Issue of Apr. 15, pp. 11563-11571 (1994).

\* cited by examiner

SEQUENCE LISTING

```
<160> NUMBER OF SEQ ID NOS: 22

<210> SEQ ID NO 1
<211> LENGTH: 16
<212> TYPE: DNA
<213> ORGANISM: Escherichia coli

<400> SEQUENCE: 1
tggcacagat tttgct                                                    16

<210> SEQ ID NO 2
<211> LENGTH: 16
<212> TYPE: DNA
<213> ORGANISM: Artificial Sequence
<220> FEATURE:
<223> OTHER INFORMATION: Consensus sequence
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 2
tggcacnnww nttgcw                                                    16

<210> SEQ ID NO 3
<211> LENGTH: 31
<212> TYPE: DNA
<213> ORGANISM: Escherichia coli

<400> SEQUENCE: 3
cttggttttt ccaagtggca cagattttgc t                                   31

<210> SEQ ID NO 4
```

```
<211> LENGTH: 31
<212> TYPE: DNA
<213> ORGANISM: Escherichia coli

<400> SEQUENCE: 4
ccctcttttt gagggagcaa aatctgtgcc a                               31

<210> SEQ ID NO 5
<211> LENGTH: 31
<212> TYPE: DNA
<213> ORGANISM: Artificial Sequence
<220> FEATURE:
<223> OTHER INFORMATION: Scrambled sequence from E. coli

<400> SEQUENCE: 5
cttggttttt ccaagaccta gttagggttt c                               31

<210> SEQ ID NO 6
<211> LENGTH: 31
<212> TYPE: DNA
<213> ORGANISM: Artificial Sequence
<220> FEATURE:
<223> OTHER INFORMATION: Scrambled sequence from E. coli

<400> SEQUENCE: 6
ccctcttttt gagggaaac cctaactagg t                                31

<210> SEQ ID NO 7
<211> LENGTH: 16
<212> TYPE: DNA
<213> ORGANISM: Pseudomonas aeruginosa

<400> SEQUENCE: 7
cgggcaacgc actgcc                                                16

<210> SEQ ID NO 8
<211> LENGTH: 15
<212> TYPE: DNA
<213> ORGANISM: Artificial Sequence
<220> FEATURE:
<223> OTHER INFORMATION: Consensus sequence
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 8
ggnanwcscn tnscn                                                 15

<210> SEQ ID NO 9
<211> LENGTH: 31
<212> TYPE: DNA
<213> ORGANISM: Pseudomonas aeruginosa
```

<400> SEQUENCE: 9
cttggttttt ccaagcgggc aacgcactgc c                                      31

<210> SEQ ID NO 10
<211> LENGTH: 31
<212> TYPE: DNA
<213> ORGANISM: Pseudomonas aeruginosa

<400> SEQUENCE: 10
ccctcttttt gagggggcag tgcgttgccc g                                      31

<210> SEQ ID NO 11
<211> LENGTH: 30
<212> TYPE: DNA
<213> ORGANISM: Artificial Sequence
<220> FEATURE:
<223> OTHER INFORMATION: Scrambled sequence from P. aeruginosa

<400> SEQUENCE: 11
cttggttttt ccaagtcaag agggccccccc                                       30

<210> SEQ ID NO 12
<211> LENGTH: 30
<212> TYPE: DNA
<213> ORGANISM: Artificial Sequence
<220> FEATURE:
<223> OTHER INFORMATION: Scrambled sequence from P. aeruginosa

<400> SEQUENCE: 12
ccctcttttt gagggggggg gccctcttga                                        30

<210> SEQ ID NO 13
<211> LENGTH: 16
<212> TYPE: DNA
<213> ORGANISM: Klebsiella pneumoniae

<400> SEQUENCE: 13
tggcacagat ttcgct                                                       16

<210> SEQ ID NO 14
<211> LENGTH: 16
<212> TYPE: DNA
<213> ORGANISM: Artificial Sequence
<220> FEATURE:
<223> OTHER INFORMATION: Consensus sequence
<220> FEATURE:
<221> NAME/KEY: misc_feature
<222> LOCATION: (4)..(9)
<223> OTHER INFORMATION: n is a, c, g, or t

<400> SEQUENCE: 14
tggnnnnnnw tttgcw                                                       16

<210> SEQ ID NO 15
<211> LENGTH: 31
<212> TYPE: DNA
<213> ORGANISM: Klebsiella pneumoniae

<400> SEQUENCE: 15
cttggttttt ccaagtggca cagatttcgc t                                      31

<210> SEQ ID NO 16
<211> LENGTH: 31
<212> TYPE: DNA

<213> ORGANISM: Klebsiella pneumoniae

<400> SEQUENCE: 16
ccctcttttt gagggagcga aatctgtgcc a                              31

<210> SEQ ID NO 17
<211> LENGTH: 31
<212> TYPE: DNA
<213> ORGANISM: Artificial Sequence
<220> FEATURE:
<223> OTHER INFORMATION: Scrambled sequence from K. pneumoniae

<400> SEQUENCE: 17
cttggttttt ccaagctaca tttagcggtg c                              31

<210> SEQ ID NO 18
<211> LENGTH: 31
<212> TYPE: DNA
<213> ORGANISM: Artificial Sequence
<220> FEATURE:
<223> OTHER INFORMATION: Scrambled sequence from K. pneumoniae

<400> SEQUENCE: 18
ccctcttttt gaggggcacc gctaaatgta g                              31

<210> SEQ ID NO 19
<211> LENGTH: 10
<212> TYPE: PRT
<213> ORGANISM: Artificial Sequence
<220> FEATURE:
<223> OTHER INFORMATION: Antimicrobial peptide

<400> SEQUENCE: 19

Ile Lys Phe Leu Lys Phe Leu Lys Phe Leu
1               5                   10

<210> SEQ ID NO 20
<211> LENGTH: 16
<212> TYPE: DNA
<213> ORGANISM: Artificial Sequence
<220> FEATURE:
<223> OTHER INFORMATION: Consensus sequence

<400> SEQUENCE: 20
tggcacacat attgca                                               16

<210> SEQ ID NO 21
<211> LENGTH: 31
<212> TYPE: DNA
<213> ORGANISM: Artificial Sequence
<220> FEATURE:
<223> OTHER INFORMATION: Gram-negative_Sig DB sequence

<400> SEQUENCE: 21
cttggttttt ccaagtggca cacatattgc a                              31

<210> SEQ ID NO 22
<211> LENGTH: 31
<212> TYPE: DNA
<213> ORGANISM: Artificial Sequence
<220> FEATURE:
<223> OTHER INFORMATION: Gram-negative_Sig DB sequence

<400> SEQUENCE: 22
ccctcttttt gagggtgcaa tatgtgtgcc a                              31

TRANSCRIPTION FACTOR DECOYS

This application claims priority to and the benefit of applications No. 1005545.7 (GB) and 61/320,195 (US), both filed 1 Apr. 2010, both of which are hereby incorporated by reference to the fullest extent allowed by law.

Applicant hereby requests that the sequence listing filed with the application is entered into the present application.

The present invention relates to antibacterial compositions, particularly compositions active against pathogenic bacteria, the compositions comprising decoy nucleic acid sequences.

The ever-increasing incidence of often multi-drug resistance among a wide range of bacterial pathogens, both in the hospital environment and in the community at large, has led to an urgent need for the discovery and development of new anti-bacterial drugs, commonly referred to as antibiotics. The severity of the problem is being exacerbated by the decline in the numbers of new drugs coming to the market or under development. This is as the pharmaceutical industry has substantially withdrawn from antibiotic discovery (Projan [2008] *Drug Discovery Today* 13: 279-280), largely reflecting the disappointing results of two decades of target-based screening combined with synthetic libraries of compounds lacking drug-like characteristics. The problem is also exacerbated by the smaller return on investment for drugs used to treat acute, rather than chronic and life-style diseases. This potentially dire situation has led the World Health Organisation to declare "Today we are witnessing the emergence of drug resistance along with a decline in the discovery of new antibacterials. As a result, we are facing the possibility of a future without effective antibiotics. This would fundamentally change the way modern medicine is practiced." (WHO (2004) *Priority Medicines for Europe and the World*).

Perhaps of most concern are the Gram-negative infections, such as those caused by the pathogenic species *Escherichia coli, Pseudomonas aeruginosa, Klebsiella pneumoniae, Acinetobacter baumanii* and other Gram-negative bacilli bacteria. Gram-negative bacteria are of particular concern because their outer cell wall protects them against most of the antibiotics, detergents and chemicals used as treatments. This outer cell wall consists of a lipid bilayer and is a selective permeable barrier that excludes compounds with molecular weights above 800. However, many small molecules pass through the outer membrane by way of various types of pores.

As a result, many commonly used antibiotics are not effective against Gram-negative bacteria. Fortunately, there are a few antibiotics which work against them, but this small number of therapies—and the clinical pressure to deliver treatments, with the concomitant danger of misuse—makes the rise of resistance more likely to happen and more difficult to cope with when it does (Rice [2009] *Curr. Opin. Microbiol.* 12: 476-481). For example *E. coli* strains have began to emerge with resistance to most beta-lactamases, termed Extended Spectrum beta-lactamases *E. coli* [ESBL *E. coli*], that are prevalent worldwide (Zahar et al. [2009] *Curr. Opin. Invest. Drugs* 10: 172-180). Strains of ESBL-*K. pneumoniae* are also widespread (Jacoby [1998] *Clin. Infect. Dis.* 27: 81-83) and these bacteria have additionally acquired resistance to other the other antibiotics such as carbapenems and tigecyclines (Lee et al. [2009] *J. Clin. Microbiol.* 47: 1611-1612), making them exceedingly difficult to treat. *A. baumanni* and *P. aeruginosa* infections are the most difficult to treat and commonly have acquired ESBL resistance, have numerous efflux pumps (that remove antibiotics from the cell) and have mechanisms that allow them to rapidly acquire genes encoding novel resistance mechanisms (Crespo et al. [2004] *J. Clin. Microbiol.* 42: 5094-5101; Fournier et al. [2006] *PLoS Genet.* 2: e7). An indication of the seriousness of the situation and the rapidity of its spread is that new terms are required to quantify the prevalence of drug-resistance in Gram-negative strains. Multiple-drug resistant [MDR] has been superseded by extreme-drug resistant [XDR], a term that was first used for *Mycobacterium tuberculosis* infections (Morb. Mortal. Wkly. Rep. [2006]55: 301-305) and recently for *A. baumanni* (Doi et al. [2009] *Emerg. Infect. Dis.* 15: 980-982). The term MDR is used to describe infections with very few treatment options, whilst the term pan-drug resistant [PDR], is used to describe infections with markedly decreased susceptibility to all treatments (Paterson & Doi [2007] *Clin. Infect. Dis.* 45: 1179-1181).

A reflection of the paucity of therapeutic options to treat drug-resistant Gram-negative infections is the return to the use of polymyxin-based drugs, such as Colistin (Falagas & Kasiakou [2005] *Clin. Infect. Dis.* 40: 1333-1341). Polymyxins are used in spite of the drugs having known issues of toxicity (Nation & Li [2009] *Clin. Opin. Infect. Dis.* 22: 535-543). There is also reliance on tigecycline (Hoban et al. [2007] *Diagn. Microbio. Infect. Dis.* 57: 423-428), which is itself subject to resistance (Dean et al. [2003] *Antimicrob. Agents Chemother.* 47: 972-973; Livermore [2009] *J. Antimicrob. Chemother.* 61: i29-i36). Hence, there is a general need for new anti-bacterial compounds and a pressing need for antibacterials with activity against Gram-negative infections. The ideal candidates would show activity against drug-resistant infections and, crucially, be less susceptible to the rise of resistance themselves. Antibacterials that have multiple, novel targets would satisfy these criteria but traditional sources of antibiotics are unlikely to deliver such molecules (Payne et al. [2007] *Nat. Rev. Drug Disc.* 6: 29-40). Increasingly pharmaceutical companies are exploring the potential of biologic therapies, such as antibodies (*Nature Rev. Drug Disc* [2010]9:177-178) and nucleic acid-based therapeutics (Geller [2005] *Curr. Opin. Mol. Ther.* 7:109-113).

DNA-based therapies have the potential to overcome the limitations of existing antibacterial therapies because they can be designed to treat potentially any pathogen either by preventing expression of genes encoding an antibiotic resistance mechanism or by inhibiting growth by modifying the expression of essential or adaptive genes or operons or similarly preventing the onset of virulence or pathogenicity. In addition, bacteria are unlikely to develop resistance to these agents as this would require simultaneous mutations that affected both the transcription factor and its cognate binding site(s). This is particularly true for agents that control several essential genes. Alternatively a gene could evade transcriptor factor decoy-mediated control by mutation so that the gene is expressed constitutively. However, in the case of a transcriptor factor decoy that acts simultaneously on many genes, it would require many of those genes to acquire mutations to switch them to constitutive expression, an event that is considered unlikely.

Transcription Factor Decoys (TFDs) are one such DNA-based therapeutic. Decoy oligonucleotides are designed to mimic the binding sites of transcription factors and prevent the latter from binding to their cognate genomic targets, with a consequent modification of gene expression (Mann and Dzau (2000) *J. Clin. Investigation* 106: 1071-1075).

Other DNA-based therapeutics include plasmids containing transgenes for gene therapy, oligonucleotides for antisense and antigene applications (Crooke S. T. (1998) *Antisense Nucleic Acid Drug Dev.* 8: 115-122), ribozymes, DNAzymes, aptamers, and small interfering RNAs (siRNAs) (Stull R. A. et al (1995) *Pharm Res.* 12: 465-483; Patil S. D. and Burgess D. J. (2003) *AAPS Newsmagazine* 6: 27). Although most of the DNA-based drugs are in pre-clinical development or the early stages of clinical trials, TFDs as a class of compounds have emerged in recent years to yield extremely promising candidates for drug therapy for a wide range of diseases, including cancer, AIDS, neurological disorders such as Parkinson's disease and Alzheimer's disease, and cardiovascular disorders.

TFDs have distinct advantages over other DNA-based therapeutics. Their mechanism of action is simple and predictable—they control gene expression by sequestering transcription factors, preventing the latter from binding to promoters by flooding the cell with sufficient copies of the specific binding sequences (hence, the term "decoys"). This is in contrast to antisense strategies where targets are difficult to define due to the complex secondary structure of mRNA. In comparison to antisense approaches, TFDs have the further advantages that they act rapidly, preventing expression of genes, whereas antisense approaches deal with the consequences of expression. As a result, TFDs are effective at much lower concentrations, because a single TFD-transcription factor interaction can block transcription of a single gene that otherwise may have given rise to many thousands of copies of mRNA, which constitute the targets for the antisense approach.

TFDs also have advantages over both traditional antibacterials and other types of biologics, including antibodies and antisense molecules, because they act on multiple, novel targets. The novelty of the targets ensures that the treatments will not be susceptible to extant resistance mechanisms nor can resistance be readily acquired by the pathogen due to horizontal gene transfer. That they can act on multiple targets (sets of co-ordinately regulated genes) greatly reduces the chances of resistance arising as it would require the acquisition of multiple mutations at each, or the majority, of targets.

TFDs are nucleic acids that contain the binding site for a transcription factor. When introduced into cells, they act as competitive inhibitors for the binding of the transcription factor to its genomic target and so modify the regulation of a targeted gene. In a therapeutic context, the targeted gene occurs in pathogenic bacteria and is essential for growth, environmental adaptation or onset of pathogenicity.

An example of a class of bacterial-specific transcription factors that control adaptive responses necessary for the bacteria to grow and cause disease inside the animal host are the alternative sigma factors (Kazmiecrzak et al. [2005] *Microbiol. Mol. Rev.* 69: 527-543; Gruber & Gross [2003] *Ann. Rev. Microbiol.* 57: 441-460; Helman [2002] *Adv. Microb. Physiol.* 46: 47-100). Sigma factors bind prokaryotic RNA polymerase and initiate transcription. Cells have one major housekeeping sigma factor and a variable number of alternative sigma factors that possess different promoter-recognition properties. The cell can choose from its repertoire of sigma factors to alter its transcriptional program, for example in response to stress. In bacteria, sigma factors can be divided into two classes on the basis of homology to either the *E. coli* sigma-70 factor [$\sigma^{70}$], which includes the major or housekeeping sigma factor, and a much smaller class with homology to the *E. coli* sigma-54 factor ($\sigma^{54}$) (Gross et al. (eds.) [1992] Transcriptional Regulation, Cold Spring Harbour Laboratory Press, p 129-176). Some $\sigma^{54}$-like proteins are also known as $\sigma^{N}$ (sigN) or RpoN because their discovery was first linked to nitrogen starvation (Merrick (1993) *Mol. Microbiol.* 10: 903-909). The $\sigma^{54}$-like proteins are the most phylogenetically distinct of the sigma factors, with a separate mechanism of initiating transcription (Buck et al. [2000] *J. Bac.* 182: 4129-4136) and, although they are widely distributed through all Gram-negative bacteria, they are usually limited to a single orthologue, whereas there are several to dozens of orthologues of the $\sigma^{70}$-proteins (Gruber & Gross [2003] *Ann. Rev. Microbiol.* 57: 441-460). The $\sigma^{70}$-like sigma factors recognise promoter sequences with conserved elements centred on 35 and 10 nucleotides upstream from the transcriptional start site, referred to as −35/−10 sequence (Thony & Hennecke [1989] *FEMS Microbiol. Rev.* 63: 341-358). The $\sigma^{54}$-like proteins recognise conserved elements located approximately 24 and 12 nucleotides upstream from the transcriptional start site, referred to as −24/−12 sequence (Barrios et al. [1999] *Nucl. Acids Res.* 17: 4305-4315). The majority of bacterial genes are under control of the −35/−10 consensus, including all of the housekeeping genes that are constitutively expressed. These genes are therefore not ideal candidates for regulation by TFDs that work optimally on genes that are induced and essential for growth or necessary for pathogenicity. Hence, those genes controlled by sigma factors recognising the −24/−12 regulatory sequences are preferred. Examples of these $\sigma^{54}$-like proteins in pathogenic bacteria are given in Merrick [1993] *Mol. Microbiol.* 10: 903-909.

Genetic deletion of alternative sigma factors implicated in mediating stress response in selected pathogenic bacteria have been shown to result in reduced growth, reduced viability and lower rates of infections of in animal models: deletion of rpoN from *P. aeruginosa* led to decreased virulence in mouse models (Hendrickson [2001] *J. Bac.* 183: 7126-7134); RpoN *Vibrio cholerae* mutants were less virulent in an infant mouse competition model (Klose & Mekalanos [1998] *Mol. Microbiol.* 28: 501-520); virulence genes necessary for flagellar formation are regulated by RpoN in *Heliobacter pylori* (Niehus et al. [2004] *Mol. Micro.* 52: 947-961); genetic studies also reveal RpoN to be an important regulator of stress and virulence in *E. coli* (Riordan et al. [2010] *Microbiol.* 156: 501-520).

It is against this background that the present invention has been devised. In particular, the present invention resides in a decoy nucleic acid sequence comprising a sequence encoding all or part of a binding site for bacterial alternative sigma54 factor, or a variant or analogue thereof. The decoy sequence of the present invention is generally termed a Transcription Factor Decoy (TFD). The term bacterial alternative sigma54 factor refers to the sigma factor also known as $\sigma^{N}$ (sigN) or RpoN. The three terms are used interchangeably throughout the specification to denote the same entity.

Ideally, the decoy sequence is derived from one or more strains of bacteria, preferably one or more strains of Gram-negative bacteria such as *E. coli*, *P. aeruginosa* and *K. pneumoniae*.

Examples of suitable decoy consensus sequences are provided in SEQ ID NO:2 (*E. coli*), SEQ ID NO:8 (*P. aeruginosa*), SEQ ID NO:14 (*K. pneumoniae*) and SEQ ID NO:20.

TFDs comprising binding site sequences for specific bacterial alternative sigma54 factors include the sequences set out in SEQ ID NO:1 and SEQ ID NOs:3 and 4 (*E. coli*), SEQ ID NO:7 and SEQ ID NOs:9 and 10 (*P. aeruginosa*), SEQ ID NO:13 and SEQ ID NOs:15 and 16 14 (*K. pneumoniae*), and SEQ ID NOs 21 and 22.

Without wishing to be bound by theory, it is believed that the process of transfection, i.e. delivering a TFD into bacterial cells through the membrane, itself stimulates a $\sigma^{54}$-mediated stress response which, when blocked by a TFD, leads to cell death. In the case of the Gram-negative pathogens, the consensus sequences for $\sigma^{54}$ binding are highly conserved and the inventor has found that a single sequence effectively kills both *E. coli* and *P. aeruginosa*, raising the prospect of developing a TFD treatment as a broad-spectrum Gram-negative antibacterial.

Once bacteria are stressed, they are far more susceptible to the activity of traditional antibiotic and antibacterial compounds. Indeed, treatment of pathogens with antibiotics triggers a stress response (Kohanski et al. [2007] *Cell* 130: 797-810), raising the possibility that TFDs that inhibit the stress response will potentiate the action of the antibiotic and may be used in combination to revive the efficacy of these traditional compounds against previously resistant strains (Dwyer et al. [2009] *Curr. Opin. Microbiol.* 12: 482-489). Thus, the present invention encompasses the use of the TFDs described above in combination with antibiotic and/or antimicrobial compounds.

Stress response genes form a class of cellular adaptive genes. These are a limited number of sets of genes, all or some of which are induced in response to a wide range of stresses. The stresses can include physical factors (temperature changes, acidity, low oxygen), biotic factors (in response to host or other bacterium) and chemical factors (such as treatment with antibiotics).

In another aspect, the TFDs of the present invention are suitable for increasing the efficacy of antibiotics generally. This includes both bacteristatic and bactericidal antibiotics.

Examples of bactericidal antibiotics include:

β-Lactams (a) Penicillins (such an ampicillin, carbenicillin and penicillin)

(b) Carbapenems (such as meropenem)

(c) Monobactams (d) Cephalosporins (such as cefepime)

First generation: Cefacetrile (cephacetrile), Cefadroxil (cefadroxyl; Duricef). Cefalexin (cephalexin; Keflex), Cefaloglycin (cephaloglycin), Cefalonium (cephalonium), Cefaloridine (cephaloradine), Cefalotin (cephalothin; Keflin), Cefapirin (cephapirin; Cefadryl), Cefatrizine, Cefazaflur, Cefazedone, Cefazolin (cephazolin; Ancef, Kefzol), Cefradine (cephradine; Velosef), Cefroxadine, Ceftezole;

Second generation: Cefaclor (Ceclor, Distaclor, Keflor, Raniclor), Cefonicid (Monocid), Cefprozil (cefproxil; Cefzil), Cefuroxime (Zinnat, Zinacef, Ceftin, Biofuroksym), Cefuzonam, Cefinetazole, Cefotetan, Cefoxitin, Carbacephems: loracarbef (Lorabid), Cephamycins: cefbuperazone, cefinetazole (Zefazone), cefminox, cefotetan (Cefotan), cefoxitin (Mefoxin);

Third generation: Cefcapene, Cefdaloxime, Cefdinir (Omnicef), Cefditoren, Cefetamet, Cefixime (Suprax), Cefinenoxime, Cefodizime, Cefotaxime (Claforan), Cefpimizole, Cefpodoxime (Vantin, PECEF), Cefteram, Ceftibuten (Cedax), Ceftiofur, Ceftiolene, Ceftizoxime (Cefizox), Ceftriaxone (Rocephin), Cefoperazone (Cefobid), Ceftazidime (Fortum, Fortaz), Oxacephems: latamoxef (moxalactam);

Fourth generation: Cefclidine, Cefepime (Maxipime), Cefluprenam, Cefoselis, Cefozopran, Cefpirome, Cefquinome, Oxacephems: flomoxef Yet to be classified: Ceftobiprole, Cefaclomezine, Cefaloram, Cefaparole, Cefcanel, Cefedrolor, Cefempidone, Cefetrizole, Cefivitril, Cefmatilen, Cefinepidium, Cefovecin, Cefoxazole, Cefrotil, Cefsumide, Ceftaroline, Ceftioxide, Cefuracetime Aminoglycosides:

(a) amikacin, gentamicin, kanamycin, neomycin, netilmicin, paromomycin, rhodostreptomycin, streptomycin, tobramycin, apramycin;

(b) Anthracyclines, e.g. doxorubicin

Quinolones (a) First generation: Cinoxacin, Flumequine, Nalidixic acid, Oxolinic acid, Pipemidic acid, Piromidic acid, Rosoxacin (b) Fluoroquinolones:

1) Second generation: Ciprofloxacin, Enoxacin, Fleroxacin, Lomefloxacin, Nadifloxacin, Ofloxacin, Norfloxacin, Pefloxacin, Rufloxacin 2) Third generation: Balofloxacin, Grepafloxacin, Levofloxacin, Pazufloxacin, Sparfloxacin, Temafloxacin, Tosufloxacin 3) Fourth generation: Besifloxacin, Clinafloxacin, Garenoxacin, Gemifloxacin, Moxifloxacin, Gatifloxacin, Sitafloxacin, Trovafloxacin/Alatrofloxacin, Prulifloxacin 4) Veterinary: Danofloxacin, Difloxacin, Enrofloxacin, Ibafloxacin, Marbofloxacin, Orbifloxacin, Pradofloxacin, Sarafloxacin Glycopeptide Antibiotics:

vancomycin, teicoplanin, telavancin, bleomycin, ramoplanin, daptomycin, decaplanin and dalbavancin.

Peptide Antibiotics:

(a) Lantibiotics;

Duramycin, nisin, epidermin, actagardine, microbisporicin and mersacidin;

(b) Lipopeptides;

Cubicin, polymyxin B and variants

Streptoaramins:

Quinupristin+dalfopristin (Synercid®).

Other examples include the classes of antibiotics known as the quinolines (such a levaquin); the sulfonamides (such as Bactrim); the tetracyclines (such as tetracycline); and variously, chloramphenicol, rifampicin and Zyvox.

However, the decoys or the present invention may also be used to increase efficacy of bacteriostatic antibiotics, such as Macrolides, Ketolides, Tetracyclines, Lincosamides (e.g. clindamycin), Oxazolidinones (Linezolid).

In one aspect, decoy sequences that cause suppression of the stress response in a cell, or cause the cell to become stressed are particularly suitable for potentiating the effects of bactericidal antibiotics.

A decoy nucleic acid sequence of the invention may be an oligonucleotide sequence or a polynucleotide sequence. An oligonucleotide sequence is generally recognised as a linear sequence of up to 20 nucleotides joined by phosphodiester bonds, while a polynucleotide sequence typically has more than 20 nucleotides and maybe single or double stranded with varying amounts of internal folding. The backbone may also be modified to incorporate synthetic chemistries known either to reduce the charge of the molecule or increase its stability in biological fluids. Examples of these include peptide nucleic acids (PNA), linked nucleic acids (LNA), morpholino oligonucleotides and phosphorothioate nucleotides and combinations of these.

The sequences provided herein illustrate single strands of the binding sites. However, it will be appreciated that in nature and in the TFDs of the present invention, the sequences will be double stranded. The complementary strands to the sequences listed herein are clearly and easily derivable, for example from Molecular Cloning: A Laboratory Manual (3$^{rd}$ Edition), 2001 by Joseph Sambrook and David Russell.

Decoys of the invention may be prepared by any suitable method, such as those methods described in co-pending application PCT/GB2008/003353.

For example, dumbbells may be prepared as linear oligonucleotides and then ligated with T4 ligase. Alternatively dumbbell decoys may be prepared by PCR using appropriate primers. Each primer generally contains a portion which will form the stem loop of the dumbbell structure. PCR amplification using the primers is typically followed by restriction digest of the amplification product and ligation to form the closed circle dumbbell.

Alternatively, dumbbells can be prepared by restriction digest of a plasmid. Digestion is followed by ligation to form the closed circle dumbbell structure.

A decoy sequence may comprise a variant or analogue of a native or consensus binding sequence, which retains decoy function. A variant or analogue may be prepared by altering, for example, 1, 2, 3, 4, 5, 6, 7, 8, 9, 10 or more nucleotides in the parent sequence. For example, footprinting experiments may indicate that particular nucleotides are less crucial for transcription factor binding and might be altered.

A putative decoy sequence can be tested for ability to compete with a given transcription factor binding site by introducing a decoy polynucleotide comprising the decoy sequence into a suitable host cell. The host cell includes the target transcription factor binding site operably linked to a gene or genes whose expression can be determined directly or indirectly, e.g. by screening for a change in phenotype. Decoy function of a test sequence can be determined by screening for a change in expression of the gene(s) or a change in the phenotype. Methods for testing and researching suitable decoy sequences are described in co-pending application PCT/GB2008/003353.

In one embodiment, the present invention resides in an antibacterial complex comprising a decoy nucleic acid sequence and one or more delivery moieties, wherein the decoy nucleic acid sequence comprises a sequence encoding all or part of a bacterial alternative sigma54 factor binding site, or a variant or analogue thereof.

As set out above, the decoy may comprise a sequence derived from one or more strains of bacteria, preferably one or more strains of Gram-negative bacteria such as *E. coli, P. aeruginosa* and *K. pneumoniae*.

Examples of suitable decoy consensus sequences are provided in SEQ ID NO:2 (*E. coli*), SEQ ID NO:8 (*P. aeruginosa*), SEQ ID NO:14 (*K. pneumoniae*) and SEQ ID NO:20.

TFDs comprising binding site sequences for specific bacterial alternative sigma54 factor sequences include the sequences set out in SEQ ID NO:1 and SEQ ID NOs:3 and 4 (*E. coli*), SEQ ID NO:7 and SEQ ID NOs:9 and 10 (*P. aeruginosa*), SEQ ID NO:13 and SEQ ID NOs:15 and 16 (*K. pneumoniae*), and SEQ ID NOs 21 and 22.

The inventors have found that delivery moieties that have some antibacterial activity in their own right are ideal. In particular, the delivery moiety or moieties should show a synergistic antibacterial effect when combined with the nucleic acid sequence. In other words, the combination of the delivery moiety and the nucleic acid sequence should show an enhanced antibacterial effect when compared to the effect of the nucleic acid sequence or delivery moiety alone.

In a preferred embodiment, the delivery moiety may be selected from quaternary amine compounds and bis-aminoalkanes and unsaturated derivatives thereof, wherein the term "aminoalkanes" as used herein refers to amino groups (preferably tertiary amino groups) that form part of a heterocyclic ring.

Exemplary of such compounds are compounds of the formula (I):

$$Q\text{-}(CH_2)_p\text{-}A\text{-}(CH_2)_q\text{---}R^3 \qquad (I)$$

wherein Q is selected from:
(a) a group $Q^1$ having the formula:

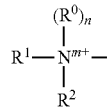

and
(b) a group $Q^2$, $Q^2$-NH—, $Q^2$-O—, or $Q^2$-S— wherein $Q^2$ is selected from monocyclic, bicyclic and tricyclic heteroaromatic groups of 5 to 14 ring members, of which 1, 2 or 3 are heteroatom ring members selected from N, O and S provided that at least one nitrogen ring member is present, wherein the heteroaromatic groups are optionally substituted by one or two substituents $R^{4a}$ and wherein the said one nitrogen ring member may form an N-oxide or may be substituted with $C_{1-4}$ alkyl, phenyl-$C_{1-4}$ alkyl or di-phenyl-$C_{1-4}$ alkyl to form a quaternary group, wherein the phenyl moieties in each case are optionally substituted with one or two halogen, methyl or methoxy groups;
m is 0 or 1;
n is 0 or 1;
p and q are the same or different and each is an integer from 1 to 12;
A is a bond or is selected from a naphthalene, biphenyl, terphenyl, phenanthrene, fluorene, stilbene, a group $C_6H_4$(CH$_2$)$_r$C$_6$H$_4$, a group C$_6$H$_4$—C≡C—C$_6$H$_4$, a pyridine-2,6-diyl-bis(benzene-1,4-diyl) group, a group CH═CH—(CH$_2$)—(CH═CH)$_t$—; and a group C≡C—(CH$_2$)$_u$—(C≡C)$_v$—; wherein r is 0-4, s is 0 to 4, t is 0 or 1; u is 0-4 and v is 0 or 1; when n is 1, $R^0$, $R^1$ and $R^2$ are each selected from $C_{1-4}$ alkyl; and when n is 0, then N, $R^1$ and $R^2$ together form a monocyclic, bicyclic or tricyclic heteroaromatic group of 5 to 14 ring members, of which one is the nitrogen atom N and 0, 1 or 2 are further heteroatom ring members selected from N, O and S, and wherein the heteroaromatic group is optionally substituted by one or two substituents $R^{4b}$; and
$R^3$ is selected from hydrogen, $C_{1-4}$ alkyl, halogen, monocyclic carbocyclic groups of 3 to 7 ring members each optionally substituted by one or two substituents $R^{4c}$, a group Q; a group —NH-$Q^2$, a group —O-$Q^2$ and a group —S-$Q^2$; and
$R^{4a}$, $R^{4b}$ and $R^{4c}$ are the same or different and each is selected from $C_{1-4}$ alkyl optionally substituted with one or more fluorine atoms: $C_{1-4}$ alkoxy optionally substituted with one or more fluorine atoms; nitro; amino; mono- and di-$C_{1-4}$ alkylamino; halogen; phenyl-$C_{1-2}$ alkyl wherein the phenyl moiety is optionally substituted with one or two methoxy, methyl or halogen substituents; ureido and guanidinyl.

In one preferred embodiment, Q is a group $Q^1$:

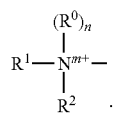

Accordingly, one preferred sub-group of compounds within formula (I) is represented by formula (II):

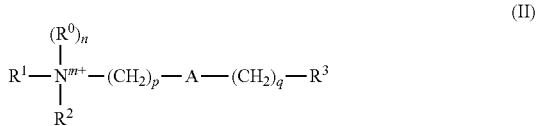

(II)

wherein $R^1$, $R^2$, m, p, A, q and $R^3$ are as defined in respect of formula (I).

One preferred sub-group of compounds within formula (II), wherein $R^3$ is $Q^1$ and n in each instance is 0, can be represented by the formula (III):

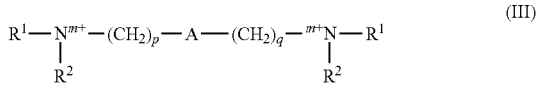

(III)

wherein $R^1$, $R^2$, m, p, A and q are as defined in respect of formula (I).

In the compounds of formulae (I), (II) and (III), when m is 1, the nitrogen atom N must be a quaternary nitrogen. Accordingly, the compounds of formulae (I), (II) and (III) wherein m is 1 will comprise one or more anions as counter ions, for example anions derived from mineral acids, sulphonic acids and carboxylic acids.

When N, $R^1$ and $R^2$ together form a monocyclic, bicyclic or tricyclic heteroaromatic group of 5 to 14 ring members, typically the group contains either the nitrogen atom N as the sole heteroatom ring member or contains a second heteroatom ring member selected from N, O and S.

When N, $R^1$ and $R^2$ together form a monocyclic, bicyclic or tricyclic heteroaromatic group, the nitrogen atom N forms part of an aromatic ring. Preferred heteroaromatic groups are monocyclic aromatic rings; bicyclic heterocyclic rings in which both rings are aromatic; bicyclic heterocyclic rings in which one nitrogen-containing ring is aromatic and the other ring is non-aromatic; and tricyclic rings in which two rings, including a nitrogen-containing ring, are aromatic and the other ring is non-aromatic.

When N, $R^1$ and $R^2$ together form a monocyclic, bicyclic or tricyclic heterocyclic group of 5 to 14 ring members, the heterocyclic group is preferably selected from quinoline; isoquinoline; acridine; tetrahydroacridine and ring homologues thereof; pyridine; benzoimidazole; benzoxazole and benzothiazole. By ring homologues of tetrahydroacridine is meant compounds containing the core structure:

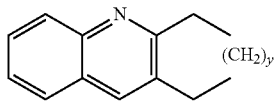

wherein y is 1 or 3. By tetrahydroacridine is meant a compound having the core structure above wherein y is 2.

In a preferred embodiment, the delivery moiety is a quaternary derivative of quinoline or acridine, in particular 1,2,3,4-tetra-hydro-9-amino-acridine. Suitable derivatives of 1,2,3,4-tetra-hydro-9-amino-acridine are described in U.S. Pat. No. 3,519,631, the contents of which are incorporated herein by reference. Of particular interest are the compounds and formulae exemplified in Examples 17 to 25 of U.S. Pat. No. 3,519,631 and analogues thereof and co-pending application PCT/GB2011/050263. Suitable qui-noline derivatives are the bis-quinolinium compounds, such as dequalinium, and analogues thereof.

Dequalinium (FIG. 1) is a bis-quinolinium compound, has mild antimicrobial properties and has been used for 30 years as an antimicrobial agent in over-the-counter mouthwashes, topical ointments, oral and vaginal paints, and sore-throat lozenges. It is a topical bacteriostat and has also been tested as an inhibitor of calcium channels, an antifungal agent (Ng et al. (2007) Bioorg. Medicinal Chem. 15: 3422-3429), an inhibitor of Tuberculosis (Guiterrez-Lugo et al. (2009) J. Biomol. Screen. 14: 643-652) and as an inhibitor of Protein Kinase C (PKC; Abeywickrama et al. (2006) Bioorg. Medicinal Chem. 14: 7796-7803).

Dequalinium has also been used to deliver DNA-based therapeutics and conventional drugs, such as paxcitol, to mitochondria in in vitro experiments. In these experiments, dequalinium was prepared as bolasomes by the dry-film method. That is, dequalinium is dissolved in an organic solvent, such as methanol, dried to completion in a vacuum and re-suspended in an aqueous solution, whereupon it is sonicated to form bolasomes which are subsequently mixed with DNA to form complexes. These complexes have been shown to be capable of delivering DNA to mitochondria by a mechanism which is believed to involve fusion of the complexes with the outer membrane of the mitochondria (Weissig and Torchilin 2001 *Adv. Drug Delivery Rev.* 49: 127-149; Weissig et al. 2001 *J. Control. Release* 75: 401-408). Although the membrane structure of mitochondria is not equivalent to those that occur in bacteria, it is similar. This raises the possibility that dequalinium could be suitable to deliver therapeutics to bacteria in an in vivo setting. However, the complexes formed with dequalinium are unstable over time in the presence of physiological buffers and biological fluids and to dilution.

Therefore, in a particularly preferred embodiment, the complex comprises a dequalinium analogue. In this way, it is possible to design a dequalinium compound that has enhanced stability (both to dilution and the presence of salt) and yet has a similar or improved toxicity profiles to dequalinium. Such an analogue has been described that forms more stable complexes (Compound 7, Galanakis et al. [J. Med. Chem. (1995) 35: 3536-3546]) as tested by various physiochemical parameters such as ability to bind DNA to the exclusion of fluorescent dye SYBR-green, size of particles formed as measured by Dynamic Light Scattering and visualised with electron microscopy and their stability in elevated concentrations of salt and on dilution and storage for extended periods (Weissig et al. (2001) S. T. P. *Pharma Sciences* 11: 91-96).

Examples of dequalinium and its analogues are compounds of the formula (IV):

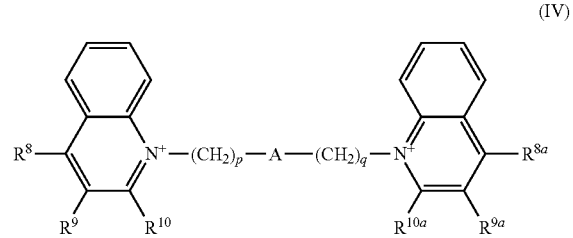

(IV)

wherein:

p and q are the same or different and each is an integer from 1 to 12;

A is a bond or is selected from naphthalene, biphenyl, terphenyl, phenanthrene, fluorene, stilbene, a group $C_6H_4(CH_2)_rC_6H_4$, a group $C_6H_4-C\equiv C-C_6H_4$, a pyridine-2,6-diyl-bis(benzene-1,4-diyl) group, a group $CH=CH-(CH_2)_s-(CH=CH)_t-$; and a group $C\equiv C-(CH_2)_u-(C\equiv C)_v-$; wherein r is 0-4, s is 0 to 4, t is 0 or 1; u is 0-4 and v is 0 or 1;

$R^8$, $R^9$ and $R^{10}$ are the same or different and are each selected from hydrogen; $C_{1-4}$ alkyl optionally substituted with one or more fluorine atoms: $C_{1-4}$ alkoxy optionally substituted with one or more fluorine atoms; nitro; amino; mono- and di-$C_{1-4}$ alkylamino; halogen, phenyl-$C_{1-2}$ alkyl wherein the phenyl moiety is optionally substituted with one or two methoxy, methyl or halogen substituents; ureido and guanidinyl; or $R^9$ and $R^{10}$ link together to form an alkylene chain $(CH_2)_w$ wherein w is 3 to 5; and $R^{8a}$, $R^{9a}$ and $R^{10a}$ are the same or different and are each selected from hydrogen; $C_{1-4}$ alkyl optionally substituted with one or more fluorine atoms: $C_{1-4}$ alkoxy optionally substituted with one or more fluorine atoms; nitro; amino; mono- and di-$C_{1-4}$ alkylamino; halogen, phenyl-$C_{1-2}$ alkyl wherein the phenyl moiety is optionally substituted with one or two methoxy, methyl or halogen substituents; ureido and guanidinyl; or $R^{9a}$ and $R^{10a}$ link together to form an alkylene chain $(CH_2)_w$ wherein w is 3 to 5.

Within formula (IV), one subset of compounds is the subset in which A is a bond, a group $CH=CH-(CH_2)_s-(CH=CH)_t-$; or a group $C\equiv C-(CH_2)_u-(C\equiv C)_v-$. Within this sub-set, preferably A is a bond, i.e. there is a saturated alkylene chain extending between the nitrogen atoms of the two quinoline rings.

When A is a bond, typically the sum of p and q is in the range from 3 to 22, preferably in the range from 6 to 20, and more preferably from 8 to 18. Particular examples are compounds in which p+q=8, or p+q=9, or p+q=10, or p+q=11, or p+q=12, or p+q=13, or p+q=14, or p+q=15, or p+q=16, or p+q=17 or p+q=18.

In each of the foregoing embodiments and subsets of compounds, $R^8$ and $R^{8a}$ are preferably each selected from hydrogen; $C_{1-4}$ alkoxy; nitro; amino; mono- and di-$C_{1-4}$ alkylamino; and guanidinyl.

More preferably, $R^8$ and $R^{8a}$ are each selected from hydrogen; $C_{1-4}$ alkoxy; amino and guanidinyl.

Still more preferably, $R^8$ and $R^{8a}$ are each selected from methoxy and amino.

In one embodiment, $R^8$ and $R^{8a}$ are both amino.

In another embodiment, $R^8$ and $R^{8a}$ are both methoxy.

In another embodiment, $R^8$ and $R^{8a}$ are both guanidinyl.

In each of the foregoing embodiments and subsets of compounds, preferably:

$R^9$ is hydrogen;
$R^{9a}$ is hydrogen;
$R^{10}$ is selected from hydrogen; amino; and $C_{1-4}$ alkyl optionally substituted with one or more fluorine atoms;
$R^{10a}$ is selected from hydrogen; amino; and $C_{1-4}$ alkyl optionally substituted with one or more fluorine atoms;
or $R^9$ and $R^{10}$ link together to form an alkylene chain $(CH_2)_w$ wherein w is 3 to 5: and/or
$R^{9a}$ and $R^{10a}$ link together to form an alkylene chain $(CH_2)_w$ wherein w is 3 to 5.

More preferably:
$R^9$ is hydrogen;
$R^{9a}$ is hydrogen;
$R^{10}$ is selected from hydrogen; amino; methyl and trifluoromethyl;
$R^{10a}$ is selected from hydrogen; amino; methyl and trifluoromethyl;
or $R^9$ and $R^{10}$ link together to form an alkylene chain $(CH_2)_w$ wherein w is 3 to 5: and/or
$R^{9a}$ and $R^{10a}$ link together to form an alkylene chain $(CH_2)_w$ wherein w is 3 to 5.

In one particularly preferred group of compounds within formula (IV):

A is a bond;
the sum of p and q is in the range from 8 to 18;
$R^8$ and $R^{8a}$ are each selected from hydrogen; $C_{1-4}$ alkoxy; amino and guanidinyl;
$R^9$ is hydrogen;
$R^{9a}$ is hydrogen;
$R^{10}$ is selected from hydrogen; amino; and $C_{1-4}$ alkyl optionally substituted with one or more fluorine atoms;
$R^{10a}$ is selected from hydrogen; amino; and $C_{1-4}$ alkyl optionally substituted with one or more fluorine atoms;
or $R^9$ and $R^{10}$ link together to form an alkylene chain $(CH_2)_w$ wherein w is 3 to 5: and/or
$R^{9a}$ and $R^{10a}$ link together to form an alkylene chain $(CH_2)_w$ wherein w is 3 to 5.

In another particularly preferred group of compounds within formula (IV):

A is a bond;
the sum of p and q is in the range from 8 to 18;
$R^8$ and $R^{8a}$ are each guanidinyl;
$R^9$ is hydrogen;
$R^{9a}$ is hydrogen;
$R^{10}$ is selected from hydrogen; amino; and $C_{1-4}$ alkyl optionally substituted with one or more fluorine atoms;
$R^{10a}$ is selected from hydrogen; amino; and $C_{1-4}$ alkyl optionally substituted with one or more fluorine atoms;
or $R^9$ and $R^{10}$ link together to form an alkylene chain $(CH_2)_w$ wherein w is 3 to 5: and/or
$R^{9a}$ and $R^{10a}$ link together to form an alkylene chain $(CH_2)_w$ wherein w is 3 to 5.

In another particularly preferred group of compounds within formula (IV):

A is a bond;
the sum of p and q is in the range from 8 to 18;
$R^8$ and $R^{8a}$ are each selected from hydrogen; $C_{1-4}$ alkoxy and amino;
$R^9$ is hydrogen;
$R^{9a}$ is hydrogen;
$R^{10}$ is selected from hydrogen; amino; and $C_{1-4}$ alkyl optionally substituted with one or more fluorine atoms;
$R^{10a}$ is selected from hydrogen; amino; and $C_{1-4}$ alkyl optionally substituted with one or more fluorine atoms;
or $R^9$ and $R^{10}$ link together to form an alkylene chain $(CH_2)_w$ wherein w is 3 to 5: and/or
$R^{9a}$ and $R^{10a}$ link together to form an alkylene chain $(CH_2)_w$ wherein w is 3 to 5.

Within this group, more preferred compounds are those in which:

A is a bond;
the sum of p and q is in the range from 8 to 18;
$R^8$ and $R^{8a}$ are each selected from hydrogen; methoxy and amino;
$R^9$ is hydrogen;
$R^{9a}$ is hydrogen;
$R^{10}$ is selected from hydrogen; amino; methyl; and trifluoromethyl;
$R^{10a}$ is selected from hydrogen; amino; methyl; and trifluoromethyl;
or $R^9$ and $R^{10}$ link together to form an alkylene chain $(CH_2)_w$ wherein w is 3 to 5: and/or $R^{9a}$ and $R^{10a}$ link together to form an alkylene chain $(CH_2)_w$ wherein w is 3 to 5.

Within formula (IV), one preferred group of compounds may be represented by the formula (V):

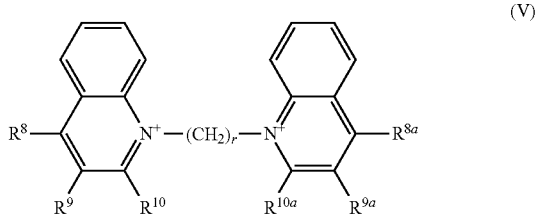

(V)

wherein:

r is an integer from 2 to 24;

$R^8$, $R^9$ and $R^{10}$ are the same or different and are each selected from hydrogen; $C_{1-4}$ alkyl optionally substituted with one or more fluorine atoms: $C_{1-4}$ alkoxy optionally substituted with one or more fluorine atoms; nitro; amino; mono- and di-$C_{1-4}$ alkylamino; halogen, phenyl-$C_{1-2}$ alkyl wherein the phenyl moiety is optionally substituted with one or two methoxy, methyl or halogen substituents; ureido and guanidinyl; or $R^9$ and $R^{10}$ link together to form an alkylene chain $(CH_2)_w$ wherein w is 3 to 5; and $R^{8a}$, $R^{9a}$ and $R^{10a}$ are the same or different and are each selected from hydrogen; $C_{1-4}$ alkyl optionally substituted with one or more fluorine atoms: $C_{1-4}$ alkoxy optionally substituted with one or more fluorine atoms; nitro; amino; mono- and di-$C_{1-4}$ alkylamino; halogen, phenyl-$C_{1-2}$ alkyl wherein the phenyl moiety is optionally substituted with one or two methoxy, methyl or halogen substituents; ureido and guanidinyl; or $R^{9a}$ and $R^{10a}$ link together to form an alkylene chain $(CH_2)_w$ wherein w is 3 to 5;

provided that:

(i) when $R^{10}$ and $R^{10a}$ are both hydrogen or are both methyl, and $R^9$ and $R^{9a}$ are both hydrogen, then at least one of $R^8$ and $R^{8a}$ is other than hydrogen, amino or dimethylamino; and (ii) when $R^9$ and $R^{10}$ link together to form an alkylene chain $(CH_2)_w$ wherein w is 4 and $R^{9a}$ and $R^{10a}$ link together to form an alkylene chain $(CH_2)_w$ wherein w is 4, then at least one of $R^8$ and $R^{8a}$ is other than amino.

Preferably, r is an integer from 8 to 20, more preferably 10 to 18, for example any one of 10, 12, 13, 14, 15, 16, 17 and 18.

In one group of compounds within formula (V), $R^8$ and $R^{8a}$ are selected from methoxy and guanidinyl. Within this group of compounds, $R^9$ and $R^{9a}$ typically are both hydrogen and $R^{10}$ and $R^{10a}$ typically are selected from hydrogen, methyl, trifluoromethyl and amino.

In another group of compounds within formula (V), $R^8$ and $R^{8a}$ are selected from hydrogen, amino, mono- and di-$C_{1-4}$ alkylamino; methoxy and guanidinyl; $R^9$ and $R^{9a}$ are both hydrogen and $R^{10}$ and $R^{10a}$ are both trifluoromethyl.

For example, the analogue may be 10,10'-(decane-1,10-diyl)bis(9-amino-1,2,3,4-tetrahydroacridinium) dichloride (FIG. 2). This compound is referred to in this specification as Compound 7 because of its original notation in Galanakis et al. (*J. Med. Chem.* (1995) 35: 3536-3546) where it was being investigated as a potential inhibitor of calcium channels. The compound has subsequently been tested as an agent for delivery of DNA therapeutics to mitochondria (Weissig et al. (2001) *S. T. P. Pharma Sci.* 11: 91-96) in which publication the advantageous stability of the complexes formed by the Compound 7 analogue were reported.

A further paper (Weissig et al. (2006) *J. Liposome Res.* 16: 249-264) reported that the Compound 7 analogue has lower toxicity in vitro compared to dequalinium.

As analogues of dequalinium with longer alkyl chains showed even lower toxicity, analogues with different chain lengths were considered (Weissig et al. (2006) *J. Liposome Res.* 16: 249-264). Thus, preferably, the alkyl chain of the dequalinium analogue has between 8 and 14 methyl groups, but with examples of chains containing as few as 3 methyl groups (Galankis et al (1996) *J. Med. Chem.* 39: 3592-3595) and other lipophilic cations containing as many as 36 methyl groups in the alkyl chain (Eaton et al. (2000) *Angew. Chem. Int. Ed.* 39: 4063-4067). More preferably, the alkyl chain has 10 or 12 methyl groups. As a result, an analogue of Compound 7 was designed with a 12 methyl groups in the alkyl chain, referred to herein after as Compound 7_12 (10,10'-(dodecane-1,12-diyl)bis(9-amino-1,2,3,4-tetrahydroacridinium) dichloride (FIG. 3)).

Other suitable analogues of dequalinium include:

1-decanyl-2-methyl-4-aminoquinolinium iodide
1-butyl-2-methyl-4-aminoquinolinium iodide
1,1,1-triethyl-1-(10-iododecan-1-yl)ammonium iodide
1-[1-(N,N,N-triethylammonium-1-yl)-2-methyl-4-aminoquinolinium diiodide
1,1'-(decane-1,10-diyl)bis(4-aminopyridinium) diiodide
1-(4-pentyn-1-yl)-4-aminopyridinium chloride
1,1'-(deca-4,6-diyne-1,10-diyl)bis(4-aminopyridinium) dichloride dehydrate
2,2'-N,N'-(decane-1,10-diyl)bis(2,4-diaminopyridine) [compound 8]
2,2'-N,N'-(decane-1,10-diyl)bis(2-aminopyridine)
2,2'-N,N'-(decane-1,10-diyl)bis(1-methyl-2-aminopyridinium) diiodide
1-(4-pentyn-1-yl)-2-methyl-4-aminoquinolinium iodide
1,1'-(deca-4,6-diyne-1,10-diyl)bis(4-amino-2-methylquinolinium) diiodide hydrate
1,1'-(decane-1,10-diyl)bis(quinolinium) diiodide
1,1'-(decane-1,10-diyl)bis(9-amino-1,2,3,4-tetra-hydroacridinium) dibromide hydrate
2,2'-(decane-1,10-diyl)bis(quinoline)
2,2'-(decane-1,10-diyl)bis(1-methylquinolinium) diiodide hydrate
2,2'-(decane-1,10-diyl)bis(4-methoxyquinoline)
2,2'-(decane-1,10-diyl)bis(1-methyl-4-methoxyquinolinium) diiodide
2,2'-(dodecane-1,12-diyl)bis(1-methylquinolinium) diiodide
2,2'-(decane-1,10-diyl)bis(isoquinolinium) diiodide
1,1'-(decane-1,10-diyl)bis(4-bromoisoquinolinium) diiodide
1,1'-(decane-1,10-diyl)bis(1H-benzimidazole)
1,1'-(decane-1,10-diyl)bis(3-methylbenzimidazolium) diiodide hemihydrate
1,1'-(decane-1,10-diyl)bis(2-methylbenzimidazole)
1,1'-(decane-1,10-diyl)bis(2,3-dimethylbenzimidazolium) diiodide
1,10-bis[N-(acridin-9-yl)amino]decane dihydrochloride dihydrate
1,1'-(1,10-Decanediyl)bis[4-amino-2-methyl quinolinium] diiodide
1,1'-(1,10-Decanediyl)bis[4-aminoquinolinium]diiodide
1,1'-(1,10-Decanediyl)bis[4-N,N,dimethylaminoquinolinium]diiodide
1,1'-(1,10-Decanediyl)bis[2-methylquinolinium]diiodide
1,1'-(1,10-Decanediyl)bis[quinolinium]diiodide
1,6-Bis[N-(1-methylquinolinium-2-methyl)amino]hexane diiodide
1,1'-(1,10-Decanediyl)bis[1-amino isoquinolinium]diiodide 1,1'-(1,10-Decanediyl)bis[2-methylbenzoxazolium]diiodide
1,1'-(1,10-Decanediyl)bis[2-methylbenzothiazolium]diiodide
1,1'-(1,10-Decanediyl)bis[2-amino-1-methylbenzimidazolium]diiodide
1,1'-[(E)-5-Decene-1,10-diyl]bis[4-amino-2-methylquinolinium], diiodide
1,1'-[(Z)-5-Decene-1,10-diyl]bis[4-amino-2-methylquinolinium], diiodide
1,1'-(1,12-Dodecanediyl)bis[4-amino-2-methylquinolinium], diiodide
1,1'-(1,14-Tetradecanediyl)bis[4-amino-2-methylquinolinium], diiodide
1,1'-(1,16-Hexadecanediyl)bis[4-amino-2-methylquinolinium], diiodide
N-Decyl-4-aminoquinaldinium Iodide
1,1'-[Biphenyl-3,3'-diylbis(methylene)]-bis(4-aminoquinolinium)
Dibromide Hydrate (4), 1,1'-[Biphenyl-4,4'-diylbis(methylene)]bis(4-aminoquinolinium) Ditrifluoroacetate
1,1'-(Phenanthrene-3,6-diylbis(methylene)]bis(4-aminoquinolinium) Dibromide Hydrate Ethanoate
1,1'-[Fluorene-2,7-diylbis(methylene)]-bis(4-aminoquinolinium) Ditrifluoroacetate
1,1'-[Methylenebis(benzene-1,4-diylmethylene)]bis(4-aminoquinolinium) Dibromide Hydrate
1,1'-[Ethylenebis-(benzene-1,4-diylmethylene)]bis(4-aminoquinolinium) Dibromide Hydrate
(Z)-1,1'-[Stilbene-4,4'-diylbis(methylene)]-bis(4-aminoquinolinium) Dibromide Sesquihydrate
(E)-1,1'-[Stilbene-4,4'-diylbis(methylene)]bis-(4-aminoquinolinium) Dibromide Dihydrate
1,1'-[Ethyne-1,2-diylbis(benzene-1,4-diylmethylene)]bis(4-aminoquinolinium) Dibromide Sesquihydrate
1,1'-[Propane-1,3-diylbis(benzene-1,4-diylmethylene)]bis(4-aminoquinolinium) Dibromide Hemihydrate Ethanoate
1,1'-[Pyridine-2,6-diylbis(benzene-1,4-diylmethylene)]-bis(4-aminoquinolinium) Dibromide Hydrate
1,1'-[Butane-1,4-diylbis(benzene-1,4-diylmethylene)]bis-(4-aminoquinolinium) Dibromide Hydrate
1,1'-[1, 1:4',1"-Terphenyl-4,4"-diylbis(methylene)]bis(4-aminoquinolinium) Dibromide Trihydrate
1,1'-[Naphthalene-2,6-diyl(bis(methylene)]bis(4-aminoquinolinium) Dibromide Hydrate
1,1'-[Benzene-1,4-diylbis(methylene)]-bis(4-aminoquinolinium) Dibromide Dihydrate
1,1'-[Benzene-1,3-diylbis(methylene)]bis(4-aminoquinolinium) Dibromide Hemihydrate
1,1'-(Propane-1,3-diyl)bis(4-aminoquinolinium) diiodide
1,1'-(Butane-1,4-diyl)bis(4-aminoquinolinium) diiodide
1,1'-(Pentane-1,5-diyl)bis(4-aminoquinolinium) diiodide
1,1'-(Hexane-1,6-diyl)bis(4-aminoquinolinium) diiodide
1,1'-(Octane-1,8-diyl)bis(4-aminoquinolinium) diiodide
1,1'-(Dodecane-1,12-diyl)bis(4-aminoquinolinium) dibromide hemihydrate
1,10-Bis[N-(2-methylquinolin-4-yl)amino]decane
1,12-Bis[N-(2-methylquinolin-4-yl)amino]dodecane
1,10-Bis[(2-methylquinolin-4-yl)amino]decane
1,12-Bis[(2-methylquinolin-4-yl)amino]dodecane
1,10-Bis(N-quinolin-4-ylamino)decane
4,4'-[Decane-1,10-diylbis(oxy)]bis[quinoline]
4,4'-[Decane-1,10-diylbis(thio)]bis[quinoline]
4,4'-Dodecane-1,12-diylbis[quinoline]
1,8-Bis(N-quinolin-4-yldiamino)octane
1,8-Bis[N-(1-methylquinolinium-4-yl)amino]octane Diiodide Hydrate
1,10-Bis[N-(1-methylquinolinium-4-yl)amino]decane Diiodide
4,4'-[Decane-1,10-diylbis(oxy)]bis[1-methylquinolinium] Diiodide
4,4'-[Decane-1,10-diylbis(thio)]bis[1-methylquinolinium] Diiodide Hydrate (10).
1,1'-Dimethyl-4,4'-dodecane-1,12-diylbis[quinolinium]Diiodide
4,4'-Decane-1,10-diylbis[quinoline]
1,1'-Dimethyl-4,4'-decane-1,10-diylbis[quinolinium]Diiodide
1,10-Bis[N-(1-benzylquinolinium-4-yl)amino]decane Dibromide
1,10-Bis[N-(1-benzyl-2-methylquinolinium-4-yl)amino]decane Bis(trifluoroacetate)
1,12-Bis[N-(1-benzyl-2-methylquinolinium-4-yl)amino]dodecane Bis(trifluoroacetate)
1-[N-(1-Benzyl-2-methylquinolinium-4-yl)amino]-10-[N-(2-methylquinolinium-4-yl)amino]decane Bis(trifluoroacetate)
1-[N-(1-Benzyl-2-methylquinolinium-4-yl)amino]-[2-(N-(2-methylquinolinium-4-yl)amino]dodecane Bis(trifluoroacetate)-3,5-Dimethoxybenzyl iodide
1,10-Bis[N-[1-(3,5-dimethoxybenzyl)-2-methylquinolinium-4-yl]amino]decane Bis(trifluoroacetate)
1-[N-[1-(3,5-Dimethoxybenzyl)-2-methylquinolinium-4-yl]amino]-10-[N-(2-methylquinolinium-4-yl)amino]decane Bis(trifluoroacetate)
1,1'-(3-Iodopropylidene)bis[benzene]
1,10-Bis[N-[1-(3,3-diphenylprop-1-yl)-2-methylquinolinium-4-yl]amino]decane Bis(trifluoroacetate)
4,7-Dichloro-1-methylquinolinium Iodide
1,10-Bis[N-(7-chloro-1-methylquinolinium-4-yl)amino]decane Diiodide Dihydrate
10,10'-(octane-1,8-diyl)bis(9-amino-1,2,3,4-tetrahydroacridinium) diiodide
10,10'-(dodecane-1,12-diyl)bis(9-amino-1,2,3,4-tetrahydroacridinium) diiodide
10,10'-(tetradecane-1,14-diyl)bis(9-amino-1,2,3,4-tetrahydroacridinium) diiodide
10,10'-(octadecane-1,18-diyl)bis(9-amino-1,2,3,4-tetrahydroacridinium) diiodide
5,5'-(dodecane-1,12-diyl)bis(1-amino-7,8,9,10-tetrahydro-6H-cyclohepta[b]quinolinium) diiodide
1,1'-(decane-1,10-diyl)bis(4-aminoquinolinium) diiodide
1,1'-(dodecane-1,12-diyl)bis(4-aminoquinolinium) diiodide
1,1'-(decane-1,10-diyl)bis(4-methoxyquinolinium) diiodide
1,1'-(decane-1,10-diyl)bis(2-aminoquinolinium) diiodide.

Dequalinium and its salts are commercially available, for example from (Sigma Aldrich). Methods of making suitable analogues are described in WO 97/48705, Galanakis et al. (1995) *J. Med. Chem.* 38: 595-606, Galanakis et al (1995) *J. Med. Chem.* 38: 3536-3546 and Galanakis et al (1996) *J. Med. Chem.* 39: 3592-3595, Abeywickrama et al. (2006) *Bioorganic Medicinal Chem.* 14: 7796-7803, Qin et al. (2000) *J. Med. Chem.* 43: 1413-1417, Campos Rosa et al (1996) *J. Med. Chem.* 39: 4247-4254, the contents of which are incorporated herein by reference. In particular, the synthesis of Compound 7 is described in Galanakis et al. (1995) supra and the synthesis of Compound 7_12 may be derived therefrom.

The compounds of formula (IV) and (V) may be prepared by methods analogous to the known methods for preparing dequalinium, as described and referenced above.

For example, compounds of the formulae (IV) and (V) can be prepared by the reaction of a quinoline compound of the formula (VI):

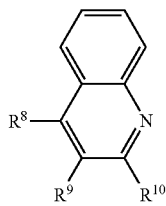
(VI)

with a compound of the formula I—(CH$_2$)$_r$—I. The reaction is typically carried out at an elevated temperature, for example in the range 120° C. to 160° C., e.g. at around 150° C.

Quinoline compounds of the formula (VI) are commercially available or can be made by standard methods well known to the skilled person or methods analogous thereto, see for example *Advanced Organic Chemistry* by Jerry March, 4$^{th}$ Edition, John Wiley & Sons, 1992, *Organic Syntheses*, Volumes 1-8, John Wiley, edited by Jeremiah P. Freeman (ISBN: 0-471-31192-8), 1995, *Fiesers' Reagents for Organic Synthesis, Volumes* 1-17, John Wiley, edited by Mary Fieser (ISBN: 0-471-58283-2), and *Handbook of Heterocyclic Chemistry*, A. R. Katritzky et al, 3$^{rd}$ Edition, Elsevier, 2010.

Compounds of the formula (VI) wherein R$^8$ is amino and R$^9$ and R$^{10}$ link together to form an alkylene chain (CH$_2$)$_w$ can be prepared by means of the following reaction sequence:

The amino group may then be converted into other functional groups by standard methods, for example by Diazotisation followed by a Sandmeyer reaction.

TFDs are effective at nanomolar concentrations and have been effective at preventing growth of bacteria in vitro and in vivo at concentrations as low as 1 nM, although it is anticipated that against certain bacteria and in more complex settings, such as in a patient higher concentrations may be needed. Hence, a preferred range would therefore be between about 10 to 100 nM, and up to around 1 µM. It will be appreciated that the range encompasses concentrations in between about 10 nM and 1 µM, such as 20 nM, 20 nM, 40 nM, 50 nM, 60 nM, 70 nM, 80 nM, 90 nM, 150 nM, 200 nM, 500 nM, 750 nM, and intermediates thereof, for example 27.2 nM.

Where the delivery moiety is a compound of any one of formulae (I) to (V) such as dequalinium or an analogue thereof, complexes are formed between the nucleic acid and the compound (e.g. dequalinium or an analogue thereof using different ratios of both. The ratio is commonly referred to as the N/P ratio (for example see Zhao et al. (2007) *Biomacromolecules* 8: 3493-3502), which defines the number of positively Nitrogen atoms in the delivery molecule per negatively charged Phosphate atom in the nucleic acid, or per nucleotide when no phosphate atoms are present. Typically complexes are formed between the compound and TFDs at N/P ratios between 0.1 and 1 (which is sufficient to achieve charge neutralisation). It will be appreciated that the present invention encompasses ratios in between 0.1 and 1, such as 0.2, 0.3, 0.4, 0.5, 0.6, 0.7, 0.8, 0.9 and intermediates thereof, e.g. 0.23.

Complexes capable of transfecting bacteria in vitro are well tolerated in animal studies. Furthermore, the components of such complexes may be used at concentrations below their known Maximum Tolerated Dose (MTD). Maximum Tolerated Dose (MTD) is the highest daily dose that does not cause overt toxicity. MIC can be estimated by animal studies as the amount of compound that, when administered to a group of test animals, has no measurable affect on long term survivability. For example, administering a complex containing 1 µM of a 100 nucleotide TFD with an N/P ratio of 1 would give a dose of approximately 3 mg/kg dequalinium analogue. It will be appreciated that this dose of dequalinium analogue is substantially below the MTD of dequalinium. The analogues of dequlanium, such as Compound 7, show less in vitro toxicity than dequalinium (Weissig et al. (2006) *J. Liposome Res.* 16: 249-264). Because dequalinium has an MTD of 15 mg/kg in mice (Gamboa-Vujicic et al. (2006) *J. Pharm. Sci.* 82: 231-235) it is predicted that the complexes should be well tolerated. It is within the reasonable skill and knowledge of the skilled person to calculate and prepare suitable concentrations.

In an alternative embodiment, the antibacterial complex comprises a nucleic acid sequence and an antibacterial peptide. The term antibacterial peptide includes and encompasses antimicrobial peptides, cell penetrating peptides, non-ribosomally synthesised peptides and glycopeptides.

Antimicrobial peptides (AMPs; also called host defence peptides) are ancient and natural antimicrobials that are diverse and widespread. They are an evolutionarily conserved component of the innate immune response and are found among all classes of life. Fundamental differences exist between prokaryotic and eukaryotic cells that may represent targets for antimicrobial peptides. These peptides are potent, broad spectrum antibiotics which demonstrate potential as novel therapeutic agents. Antimicrobial peptides have been demonstrated to kill Gram-negative and Gram-positive bacteria (including strains that are resistant to conventional antibiotics), mycobacteria (including *Mycobacterium tuberculosis*), enveloped viruses and fungi. Unlike the majority of conventional antibiotics, it appears that antimicrobial peptides may also have the ability to enhance immunity by functioning as immunomodulators.

Antimicrobial peptides are generally between 12 and 50 amino acids. These peptides include two or more positively charged residues provided by arginine, lysine or, in acidic environments, histidine, and a large proportion (generally >50%) of hydrophobic residues. The secondary structures of these molecules follow four themes, including i) α-helical, ii) β-stranded due to the presence of two or more disulfide bonds, iii) β-hairpin or loop due to the presence of a single disulfide bond and/or cyclisation of the peptide chain, and iv) extended. Many of these peptides are unstructured in free solution and fold into their final configuration upon partitioning into biological membranes. The peptides contain hydrophilic amino acid residues aligned along one side and hydrophobic amino acid residues aligned along the opposite side of a helical molecule. This amphipathicity of the antimicrobial peptides allows the peptides to partition into the membrane lipid bilayer. These peptides have a variety of antimicrobial activities ranging from membrane permeabilisation to action on a range of cytoplasmic targets.

The modes of action by which antimicrobial peptides kill bacteria is varied and includes disrupting membranes, interfering with metabolism, and targeting cytoplasmic components. The initial contact between the peptide and the target organism would be electrostatic, as most bacterial surfaces are anionic. Their amino acid composition, amphipathicity, cationic charge and size allow them to attach to and insert into membrane bilayers to form pores by 'barrel-stave', 'carpet' or 'toroidal-pore' mechanisms. Once the cell has been penetrated, the peptides bind to intracellular molecules which are crucial to cell living, thereby inhibiting cell wall synthesis, altering the cytoplasmic membrane, activating autolysin, inhibiting DNA, RNA, and protein synthesis, and inhibiting certain enzymes. However, in many cases, the exact mechanism of killing is not known. In contrast to many conventional antibiotics, these peptides appear to be bacteriocidal (bacteria killer) instead of bacteriostatic (bacteria growth inhibitor).

In the competition of bacterial cells and host cells with the antimicrobial peptides, antimicrobial peptides will preferentially interact with the bacterial cell to the mammalian cells, which enables them to kill microorganisms without being significantly toxic to mammalian cells. Since the surface of the bacterial membranes is more negatively charged than mammalian cells, antimicrobial peptides will show different affinities towards the bacterial membranes and mammalian cell membranes.

It is well known that cholesterol is normally widely distributed in the mammalian cell membranes as a membrane stabilizing agents but is absent in bacterial cell membranes. The presence of these cholesterols will also generally reduce the activities of the antimicrobial peptides, due either to stabilisation of the lipid bilayer or to interactions between cholesterol and the peptide. Thus, the cholesterol in mammalian cells will protect the cells from attack by the antimicrobial peptides.

In addition, the transmembrane potential is well-known to affect peptide-lipid interactions. A negative transmembrane potential exists between the outer leaflet to the inner leaflet of a cell membrane. This inside, negative transmembrane potential facilitates membrane permeabilisation probably by facilitating the insertion of positively charged peptides into membranes. By comparison, the transmembrane potential of bacterial cells is more negative than that of normal mammalian cells, so bacterial membrane will be prone to be attacked by the positively charged antimicrobial peptides.

As discussed above, AMPs are a unique and diverse group of molecules, which are divided into sub-groups on the basis of their amino acid composition and structure. A database of many of the known AMPs can be found at http://www.bbcm.units.it/~tossi/pag1.htm. Other groups of peptides with anti-infective properties include the non-ribosomal peptides, examples of which include gramicidin, and as a sub-group those with glycopeptides antibiotics, where peptides (which are commonly cyclic) are glycosylated. Examples of these include Polymyxin.

The present inventors have made a functional classification of all of these peptides, which are termed Anti-Bacterial Peptides (ABPs) herein, to distinguish them from AMPs, based on the mechanism of bacterial killing, and include peptides derived from other classes of antibacterials such as cell-penetrating peptides, non-ribosomally synthesised peptides and glycopeptides. It will be appreciated that the invention encompasses naturally occurring and non-naturally occurring, synthetic peptides.

Class I.

ABPs that are membrane active (Polymyxin, gramicidin) and affect entry by causing sufficient damage to punch holes in the outer membrane and allow extrusions (or 'blebs') of the bacterial inner membrane to form, through which large molecules can pass. Several of these peptides are used in the clinic but there are concerns about toxicity as they damage eukaryotic membranes as well.

The rate of resistance against antibacterial peptides is remarkably low and these peptides are widespread in nature. As this class is predominantly cationic, resistance mechanisms would take the form of changes to charge density on the outer membrane of bacteria, and such changes have been seen in the lab. Hence, the relative low incidence of resistance may reflect the fact that the ABPs are not that effective, rather than being difficult to resist.

Class II.

This is a much smaller class. These ABPs do not damage the membrane but instead have intracellular targets. Thus, the peptides must translocate through the bacterial membranes to reach their targets. As a result, they are markedly less toxic than Class I ABPs as they do not damage eukaryotic membranes causing haemolysis etc. Although they are cationic, their ability to cross membranes is not expected to be solely predicated on their charge but other broader structural properties, which largely remain undefined. As consequence, resistance mechanisms are thought less likely to occur as such mechanisms would need to alter the hydrophobic nature of the bacterial membranes themselves.

An example of an ABP that is capable of translocation is Buforin and a truncated form Buforin II (BF2). This peptide shows (weak) broad spectrum activity against pathogenic bacteria (Park et al. (2000) Proc. Natl. Acad. Sci. USA 97: 8245-8250). It has been used to translocate eukaryotic membranes and even to deliver a 28 kDa peptide (GFP) to human cell lines (Takeshima et al. (2003) J. Biol. Chem. 278: 1310-1315), although this was via endocytosis and probably due to the cationic nature of the peptide.

The ABP may be a naturally occurring peptide, such as Gramicidin, or Buforin. Alternatively, the ABP may be a peptidomimetic or a synthetic variant of a naturally occurring peptide, such as Buforin II or Polymyxin nonapeptide.

Examples of antimicrobial peptides with the ability to permeabilise biological membranes are provided in Papagianni et al ((2003) Biotechnol. Adv. 21: 465-499) and include defensins, pleuricidins, magainins, dermaseptins, apidaecins, cecropins, microcins and pediocins.

Examples of antibacterial peptides with the ability to permeabilise biological membranes are provided in Varra et al ((1992) Microbiol. Rev. 56: 395-411) and include the lantibiotics, glycopeptide antibiotics, cationic polypeptides such as polylysine and polyarginine.

Types and characteristics of ABPs are summarised in Table 1:

| Type | characteristic | ABPs |
|---|---|---|
| Anionic peptides | rich in glutamic and aspartic acids | Maximin H5 from amphibians, Dermcidin from humans |
| Linear cationic α-helical peptides | lack in cysteine | Cecropins, andropin, moricin, ceratotoxin and melittin from insects, Magainin, dermaseptin, bombinin, brevinin-1, esculentins and buforin II from amphibians, CAP18 from rabbits, LL37 from humans |

| Type | characteristic | ABPs |
|---|---|---|
| Catioinic peptide enriched for specific amino acid | rich in proline, arginine, phenylalanine, glycine, tryptophan | abaecin, apidaecins from honeybees, prophenin from pigs, indolicidin from cattle. |
| Anionic and cationic peptides that contain cysteine and form disulfide bonds | contain 1~3 disulphide bond | 1 bond: brevinins, 2 bonds: protegrin from pig, tachyplesins from horseshoe crabs, 3 bonds: defensins from humans, more than 3: drosomycin in fruit flies |
| Anionic and cationic peptide fragments of larger proteins | Generated by peptidic cleavage | Cascocidin I from human casein, lactoferricin from lactoferrin, antimicrobial domains from human haemoglobin or lysozyme |

The ABP may be linked to the nucleic acid by electrostatic or covalent linkages. In particular, where the mechanism of killing of the ABP is via intracellular targeting, rather than membrane permeabilisation, the complex may include a covalent linkage, such as a suitable linker or cross-linker between the nucleic acid sequence and the ABP. An example of a suitable linker is one that couples a carboxyl group to a primary amine. For example, a suitable linker may be EDC (1-ethyl-3-[3-dimethylaminopropyl]carbodiimide hydrochloride).

EDC is known for its use as a carboxyl activating agent for the coupling of primary amines to yield amide bonds and a common use for this carbodiimide is protein cross-linking to nucleic acids.

Although ABPs have antimicrobial activity on their own, it has been found that such peptides act synergistically when in combination with TFDs to prevent bacterial growth. Some ABPs have a bacteriostatic effect and others rapidly kill on contact. It has been found that sub-lethal concentrations of the peptides allow entry of TFDs. The peptides stress the bacteria making them more vulnerable to TFDs, which then block stress causing growth stasis or cell death.

The complexes are prepared so that the ABPs are at a concentration that is typically 5-10 fold less than their Minimum Inhibitory Concentration (MIC). The MIC of a compound is the minimum concentration of that compound to prevent visible growth of the bacteria. Typically the MIC is determined by a dilution method where inoculated cultures of bacteria are incubated overnight with a series of concentrations of the compound and the one that prevents growth is taken as the MIC. It is within the reasonable skill and knowledge of the skilled person to calculate and prepare suitable concentrations.

In a yet further embodiment, the antibacterial complex of the present invention comprises a) a decoy nucleic acid sequence, b) a quarternary amine compound or bis-aminoalkane, or an unsaturated derivative thereof, wherein the amino component of the aminoalkane is an amino group forming part of a heterocyclic ring, and c) an antibacterial peptide. The decoy nucleic acid sequence comprises a sequence encoding all or part of a binding site for bacterial alternative sigma54 factor, or a variant or analogue thereof.

Expressed in another way, the antibacterial complex of the present invention comprises a) a nucleic acid sequence, b) a quarternary derivative of quinoline or acridine, and c) an antibacterial peptide.

In a particularly preferred embodiment, the antibacterial complex comprises a) a transcription factor decoy as described above, b) a dequalinium analogue and optionally, c) an antimicrobial peptide.

In a yet further aspect, the present invention residues in use of the decoy nucleic acid sequences and complexes of the invention in a suitable formulation for the treatment of one or more bacterial infections.

In particular, the invention provides a method for treating bacterial infection in a subject comprising administering a decoy nucleic acid sequence or antibacterial complex formulated as described herein. The subject may be a human or animal. The invention also provides a decoy nucleic acid sequence or antibacterial complex formulated as described herein for use in medicine, e.g. for use in treating or preventing bacterial infection in a subject, and the use of the decoy nucleic acid sequence or antibacterial complex formulated as described herein for the manufacture of a medicament for treating bacterial infection.

The invention further relates to a pharmaceutical composition or medicament comprising a decoy nucleic acid sequence or an antibacterial complex, at least one delivery moiety and a physiologically acceptable carrier or excipient. The decoy nucleic acid sequence comprises a sequence encoding all or part of a bacterial alternative sigma54 factor binding site, or variant or analogue thereof. The delivery moiety is selected from quaternary amine compounds; bis-aminoalkanes and unsaturated derivatives thereof, wherein the amino component of the aminoalkane is an amino group forming part of a heterocyclic ring; and an antibacterial peptide. The composition may additionally comprise one or more antibiotic or other antibacterial compound or composition such as those listed above.

The number of decoy sequences needed to show a predictable effect on expression of a targeted gene and have a bacteriostatic or bacteriocidal effect can be as little as circa 5000 molecules per cell. It has been found that as many as 1,000,000 bacterial cells are efficiently killed with as little as 1 nM of TFD (PCT/GB2009/051301), suggesting that it is sufficient to have a transfection efficiency of less than 0.001% to achieve killing. In comparison with other nucleic acid-based strategies to tackle bacterial infections, such as antisense, this number of molecules needed to kill the cell is 100 to 1000-fold less. This partly reflects that although both antisense approaches and TFDs act to inhibit genes, TFDs act at an early step to prevent transcription whilst antisense, in the most common iteration, sterically blocks the products of transcription: many thousands of mRNAs molecules. Secondly, the TFDs have been designed to target essential genes that are positively induced, so need to be switched on for survival, and positively regulated (the transcription factor drives its own production). In vitro, this latter characteristic means that relatively few copies of the transcription factor are likely present when the gene is uninduced and so a small number of TFDs can block induction.

It may be that, in a therapeutic situation, there are more transcription factors per cell, due to natural variety amongst the bacterial population or the gene being already induced. In this situation it is expected that more TFDs will be needed to see a therapeutic effect and estimate that increasing the dose by a factor of 100 (to 100 nM) or improving the transfection efficiency (by two orders of magnitude) will be sufficient to see a beneficial effect. Transfection may be quantified using fluorescence microscopy (Zhang et al. (1996) *J. Mol. Neurosci.* 7: 13-28).

Pharmaceutical compositions according to the present invention, and for use in accordance with the present invention, may comprise as, or in addition to active ingredient, a pharmaceutically acceptable excipient or diluent any suitable binder, lubricant, suspending agent, coating agent, solubilising agent or other materials well known to those skilled in the art. Such materials should be non-toxic and should not interfere with the efficacy of the active ingredient. Acceptable carriers or diluents for therapeutic use are well known in the pharmaceutical art, and are described, for example, in Remington' Pharmaceutical Sciences, Mack Publishing Co. (A. R. Gennaro edit. 1985). The precise nature of the carrier or other material will depend on the route of administration, which may be oral, or by injection, e.g. cutaneous, subcutaneous or intravenous.

The active ingredient is defined as a decoy nucleic acid sequence either alone or complexed (or formulated) with a delivery moiety, the delivery moiety being the delivery moiety is selected from a quaternary derivative of quinoline or acridine and an antibacterial peptide. In the complex/formulation, the quaternary derivative of quinoline or acridine, such as dequalinium or its analogue, is in the form of a bolasome. The term 'bolasome' is used in this specification to describe vesicles of the derivative after the compound has been subjected to sonication (see Weissig and Torchilin (2001) *Adv. Drug Delivery Rev.* 49:127-149)

A variety of methods may be used to deliver the decoy or antibacterial complex of the present invention to the site of bacterial infection. Methods for in vivo and/or in vitro delivery include, but are not limited to, bucchal or oral delivery, intravenous delivery, direct injection into the infection or indirect injection (e.g. subcutaneous, intraperitoneal, intramuscular, or other injection methods), topical application, direct exposure in aqueous or media solution, transfection (e.g. calcium phosphate, electroporation, DEAE-dextran based, and lipid mediated), transgenic expression (e.g. a decoy expression system delivered by microinjection, embryonic stem cell generation, or retroviral transfer), or any of the other commonly used nucleic acid delivery systems known in the art. Administration may be in combination with a suitable dose of antibiotic, with the antibiotic(s) being administered at the same time as the nucleic acid sequence, or separately.

Pharmaceutical compositions for oral administration may be in tablet, capsule, powder or liquid form. A tablet may comprise a solid carrier such as gelatine or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, tonicity and stability. Those of relevant skill in the art are well able to prepare suitable solutions using, for example, isotonic vehicles such as sodium chloride, Ringer's injection, lactated Ringer's injection, preservatives, stabilisers, buffers, antioxidants and/or other additives may be included, as required.

For some applications, pharmaceutical formulation may not be required. For example, the antibacterial complex of the invention may be tolerated as a pharmaceutical in its own right, without the need for excipients and/or carriers.

Alternatively, the antibacterial complex may be suitable for use as an antibacterial disinfectant and so may be required in a suitable aqueous format. In which instance, the complex may further comprise aqueous and organic solvents and their combinations.

The decoy or antibacterial complex of the invention may be used to treat a variety of bacterial infections wherever they occur within the human body. Five general areas of bacterial infection can be described.

Respiratory tract infections are amongst the commonest, the upper respiratory tract infections including the ears, throat, and nasal sinuses that can be treated with tropical applications or aerosol preparations. Lower tract infections include pneumonia (which is caused by a range of bacterial pathogens, bronchitis and infective complications of cystic fibrosis.

A common problem in both community and hospital practice is urinary tract infections, where the urine becomes infected and antibacterials need to enter the bladder, prostrate, ureter and kidneys.

The gut is vulnerable to infections, where bacteria cause disease by either by mucosal invasion or toxin production, an example of which includes cholera epidemics, and when used antibiotics are either ingested or administered intravenously.

Skin and soft tissue infections, which can be treated by topical applications, are common following traumatic injury or burns, which allow colonisation and ingression of microorganisms resulting in infections that are both localised or have spread rapidly through tissues. Microbes responsible for skin infections often arise from normal skin flora, such as *Streptococcus pyogenes* causing superficial skin infections (impetigo), cellulitis (more deep-seated infection that can spread to the blood) and necrotising fasciitis, a rapidly progressive infection that is often life-threatening.

Finally infections of the central nervous system, such as bacterial meningitis, are perhaps the most challenging to treat as therapies must penetrate the blood-brain barrier, as too have the pathogenic bacteria.

The decoy or antibacterial complex of the present invention may be used in combination with one or more antibiotics to which the nucleic acid sequence makes the bacterial cell more sensitive, and/or with another antibacterial agent. Suitable antibiotics are described above and in co-pending applications WO 2009/044154 and PCT/GB2009/051301. It will be appreciated that the lists provided therein may not be exhaustive. The present invention encompasses any suitable antibiotic or antibacterial compounds or compositions.

The antibiotic or antibacterial compound may be administered simultaneously with, or before or after the antibacterial complex of the invention. The antibiotic/antibacterial compound and decoy or antibacterial complex may be administered in the same or in separate compositions. Thus the invention includes combination therapies in which a decoy or an antibacterial complex as identified, and/or as described, herein is administered to a subject in combination with one or more antibiotics or other antibacterial therapies.

The composition may additionally comprise one or more antibiotic or other antibacterial compounds or compositions.

The decoys of the present invention are suitable for use in prokaryotes generally. In particular the decoys may be used in pathogens, especially pathogenic bacteria, for example, pathogenic bacteria affecting humans. These include bacteria of the following genuses (listed according to result in the Gram stain test):

Gram negative: *Acinetobacter; Bordetella; Borrelia; Brucella; Campylobacter; Escherichia; Francisella; Haemophilus; Helicobacter; Klebsiella; Legionella; Leptospira; Neisseria; Proteobacteria; Pseudomonas; Rickettsia; Salmonella; Shigella; Treponema; Vibrio; Yersinia.*

Gram positive: *Bacillus; Clostridium; Corynebacterium; Enterococcus; Listeria; Mycobacterium; Staphylococcus; Streptococcus.*

Unstained: *Chlamydia; Mycoplasma.*

Examples of gram negative pathogenic species and of disease caused by them include: *A. barumannii* (Pneumonia, Bacteremia), *Bordetella pertussis* (whooping cough), *Borrelia burgdorferi* (Lyme's disease), *Brucella abortus* (Brucellosis), *Campylobacter jejuni* (Acute enteritis), *Coxiella burnetti* (Q Fever), *Escherichia coli* (septicemia, meningitis and pneumonia), *Francisella tularensis* (Tularemia), *Haemophilus influenzae* (Influenza and meningitis), *Helicobacter pylori* (Peptic ulcers), *Klebsiella pneumoniae* (pneumonia), *Legionella pneumophilla* (Legionnaire's disease), *Neisseria gonorrhoeae* (Gonorrhoeae), *Neisseria menigitidis* (meningitis), *Acinetobacteria* spp (Noscomia; infections), *Pseudomonas aeruginosa* (sepsis), *Rickettsia rickettsii* (Ricketts), *Salmonella typhimurium* (Typhoid), *S. dysenteriae* (Dysentery), *Vibrio cholerae* (Cholera) *Yersinia pestis* (plague).

Examples of gram positive pathogenic species and of disease caused by them include: *Bacillus anthracis* (Anthrax), *Clostridium difficile* (Pseudomembranous colitis), *Corynebacterium diptheriae* (Diptheria), *Enterococcus faecalis* (Noscomial infections), *Listeris monocytogenes* (Listerosis and meningitis), *Mycobacterium tuberculosis* (Tuberculosis), *Staphylococcus aureus* (Septicemia), *S. pneumoniae* (Pneumonia).

Bacteria of the following genuses (including the species referred to above) are particularly suitable for with the present methods: *Acientobacter, Escherichia; Helicobacter; Klebsiella; Neisseria; Proteobacter; Pseudomonas; Salmonella; Bacillus; Clostridium; Enterococcus; Staphylococcus; Shigella.*

As well as therapeutic uses, e.g. medical or veterinary, the decoys or antibacterial complexes of the present invention also have other ex vivo e.g. non-therapeutic applications, e.g. in disinfectants and cleaning products. In essence, the decoys or antibacterial complexes find use in methods where there is a need to reduce prokaryotic cell viability, kill cells, inhibit growth or reduce virulence. Thus the decoys may find use in bactericidal or bacteriostatic compositions.

Decoy nucleic acid sequences of the present invention may further be used in products that are applied to a surface, such as a work bench or hands, for a time and under conditions that are sufficient to reduce or prevent growth of a microorganism, and/or kill a microorganism, thereby reducing or preventing growth or killing a microorganism. For example, one or more decoys may be sprayed onto the surface. Such spray application is useful, for example, for preparing a surface for preparation of a foodstuff or sterilising an object to be inserted into a patient. This is because spraying the decoy formulation reduces the handling of the surface or object, thereby further reducing the risk of contamination. Hand and mouth wash applications are also contemplated within the scope of the invention.

In the above circumstances, the decoys may be formulated in a suitable aqueous format. In which instance, the formulation may comprise water to form an aqueous composition. The aqueous composition may further comprise aqueous and organic solvents and their combinations.

The invention also relates to kits for antibacterial use comprising a decoy nucleic acid sequence or an antibacterial complex as described herein and one or more antibiotics or other antibacterial agent(s) for combined use in killing or inhibiting growth or virulence of bacteria. Typically the kit includes instructions for use. Again the kit may be for therapeutic use, e.g. against bacterial infection, or for non-therapeutic use, e.g. for cleaning or disinfecting.

All documents referred to herein are hereby incorporated by reference.

Figure 1:
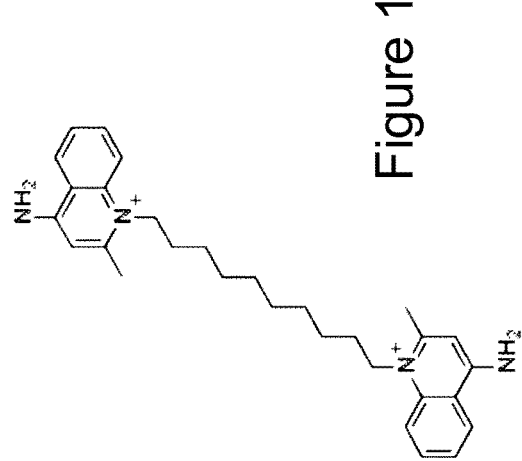

The invention will now be described in more detail by way of non-limiting examples with reference to the following figures in which:

FIG. 1. Chemical structure of Dequalinium.

FIG. 2. Chemical structure of 10,10'-(decane-1,10-diyl) bis(9-amino-1,2,3,4-tetrahydroacridinium) dichloride.

Figure 3:
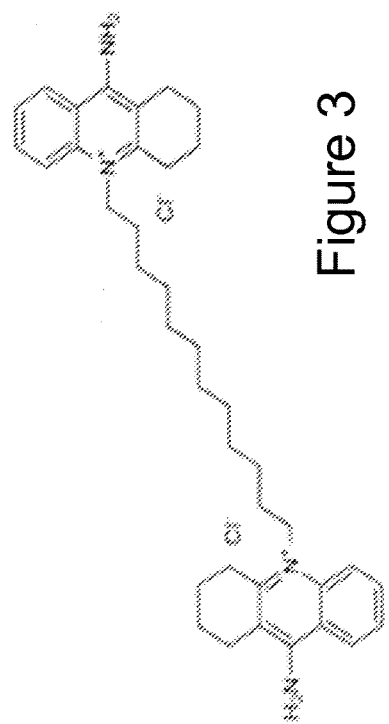

FIG. 3. Chemical structure of 10,10'-(dodecane-1,12-diyl) bis(9-amino-1,2,3,4-tetrahydroacridinium) dichloride.

Figure 4:
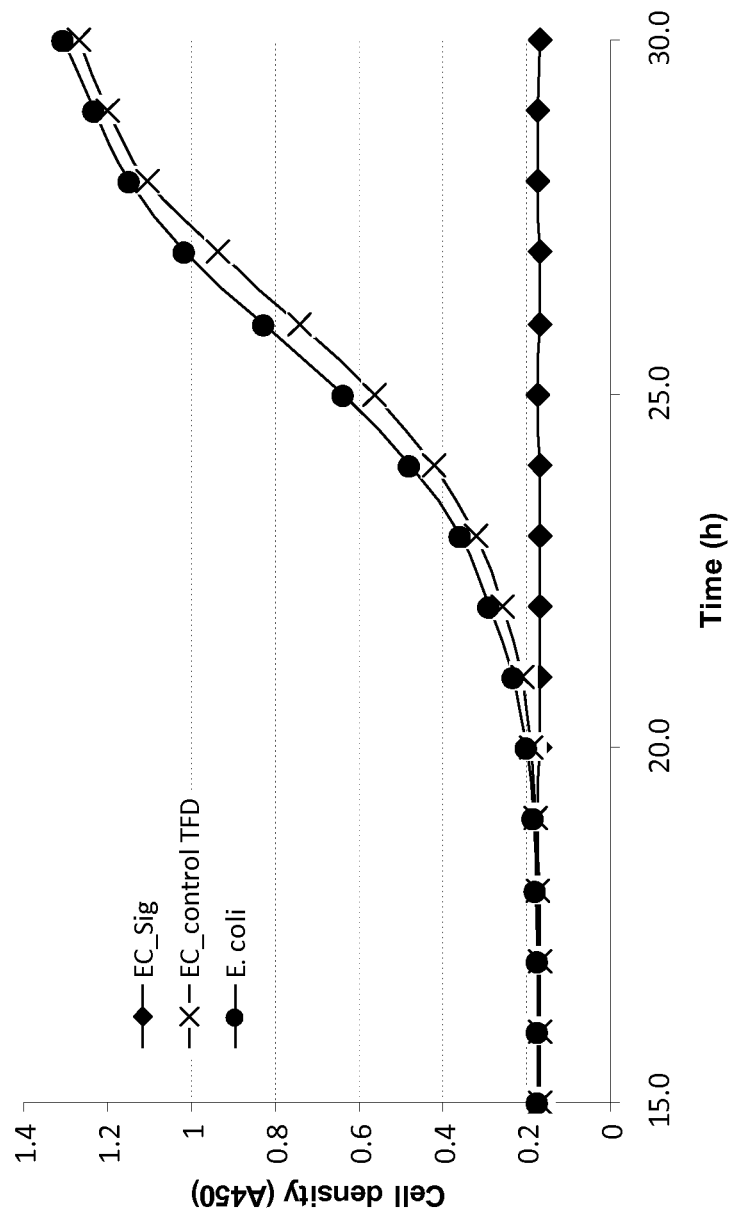

FIG. 4. Graph demonstrating growth retardation of *E. coli* with EC_Sig TFD complexes formed with Compound 7, as determined in in vitro bioassays.

Figure 5:
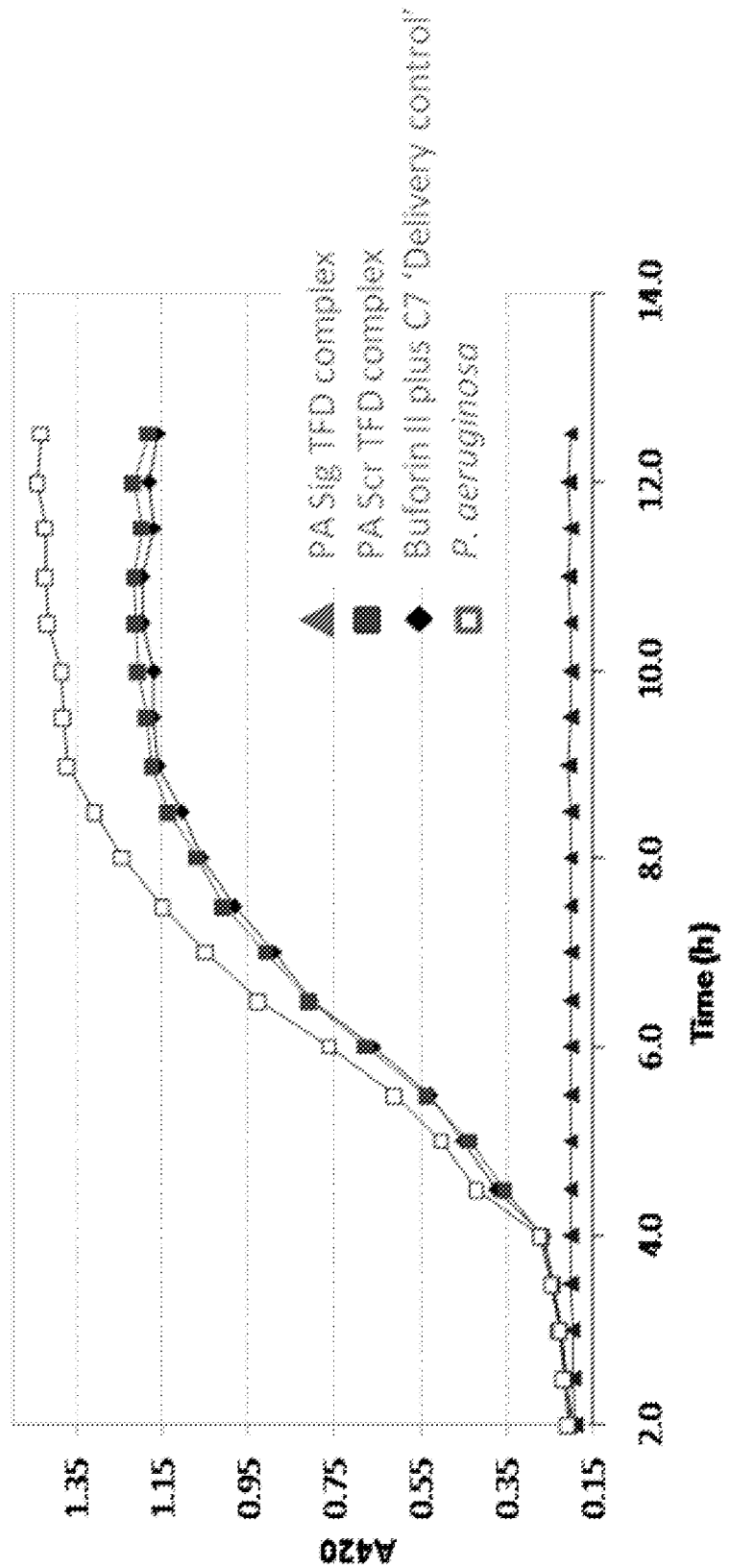

FIG. 5. Graph demonstrating growth retardation of *P. aeruginosa* with PA_Sig TFD complexes formed with Compound 7, in the presence of Buforin II, as determined in in vitro bioassays.

Figure 6:
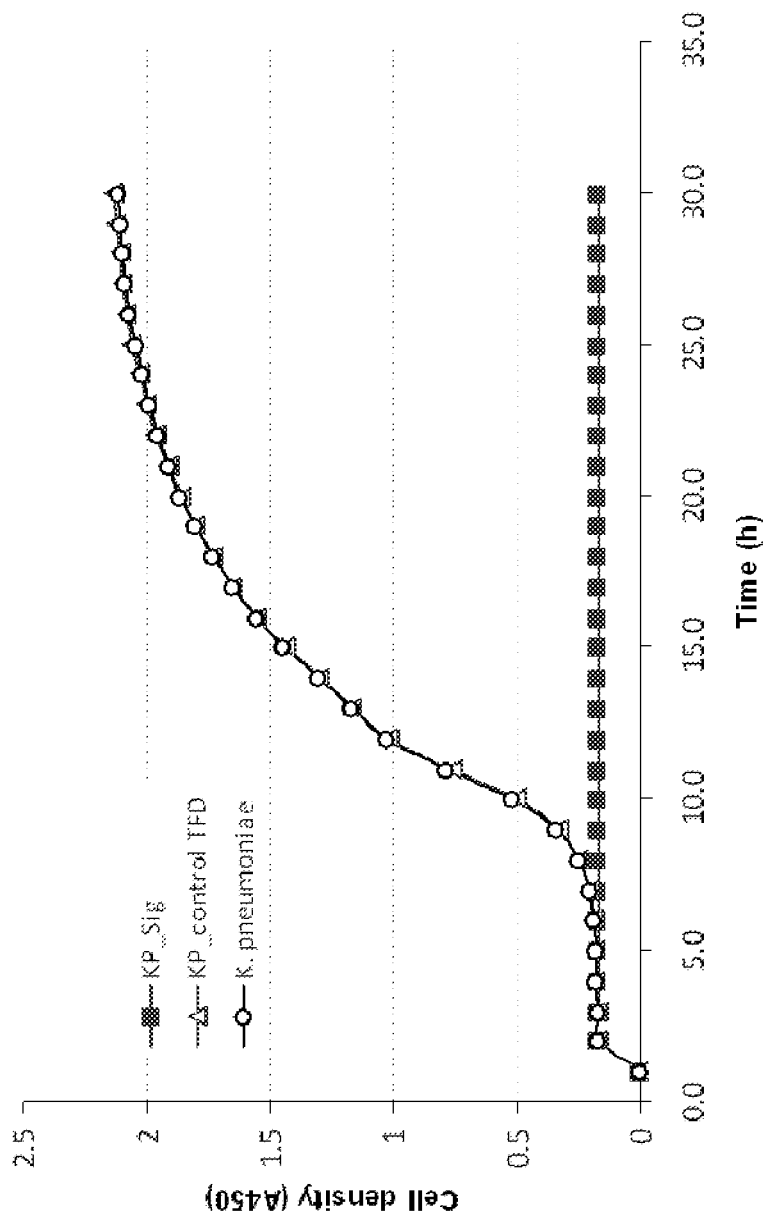

FIG. 6. Graph demonstrating growth retardation of *K. pneumoniae* with PA_Sig TFD complexes formed with Compound 7, in the presence of an antimicrobial peptide, as determined in in vitro bioassays.

Figure 7:
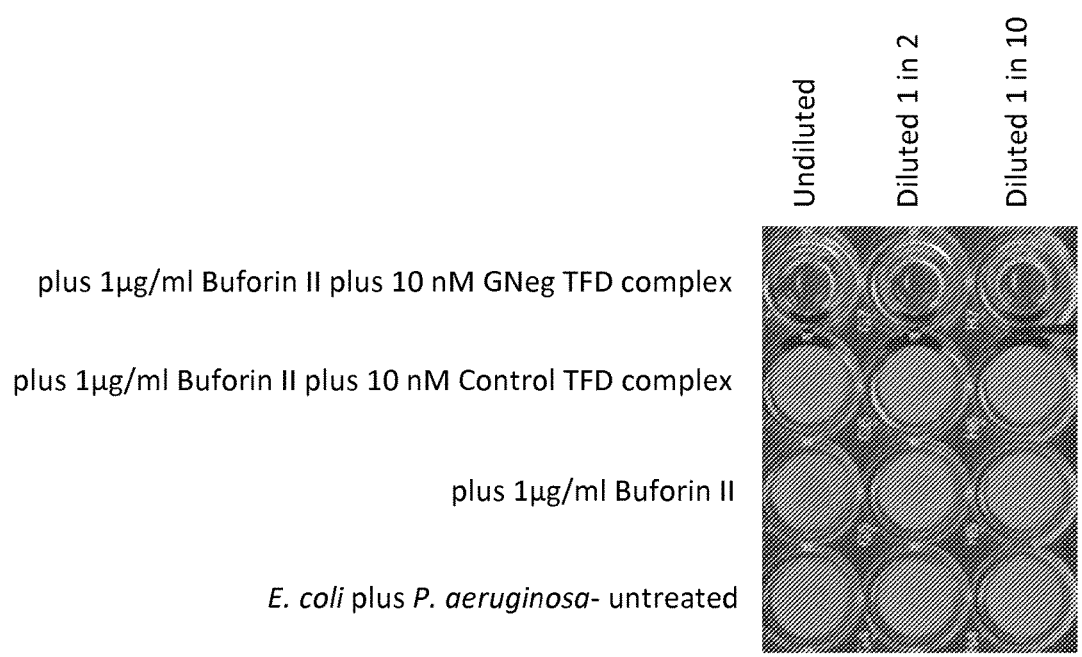

FIG. 7. In vitro bioassays demonstrating growth retardation of *E. coli* and *P. aeruginosa* with GN_Sig TFD complexes formed with Compound 7, in the presence of Buforin II.

Figure 8:
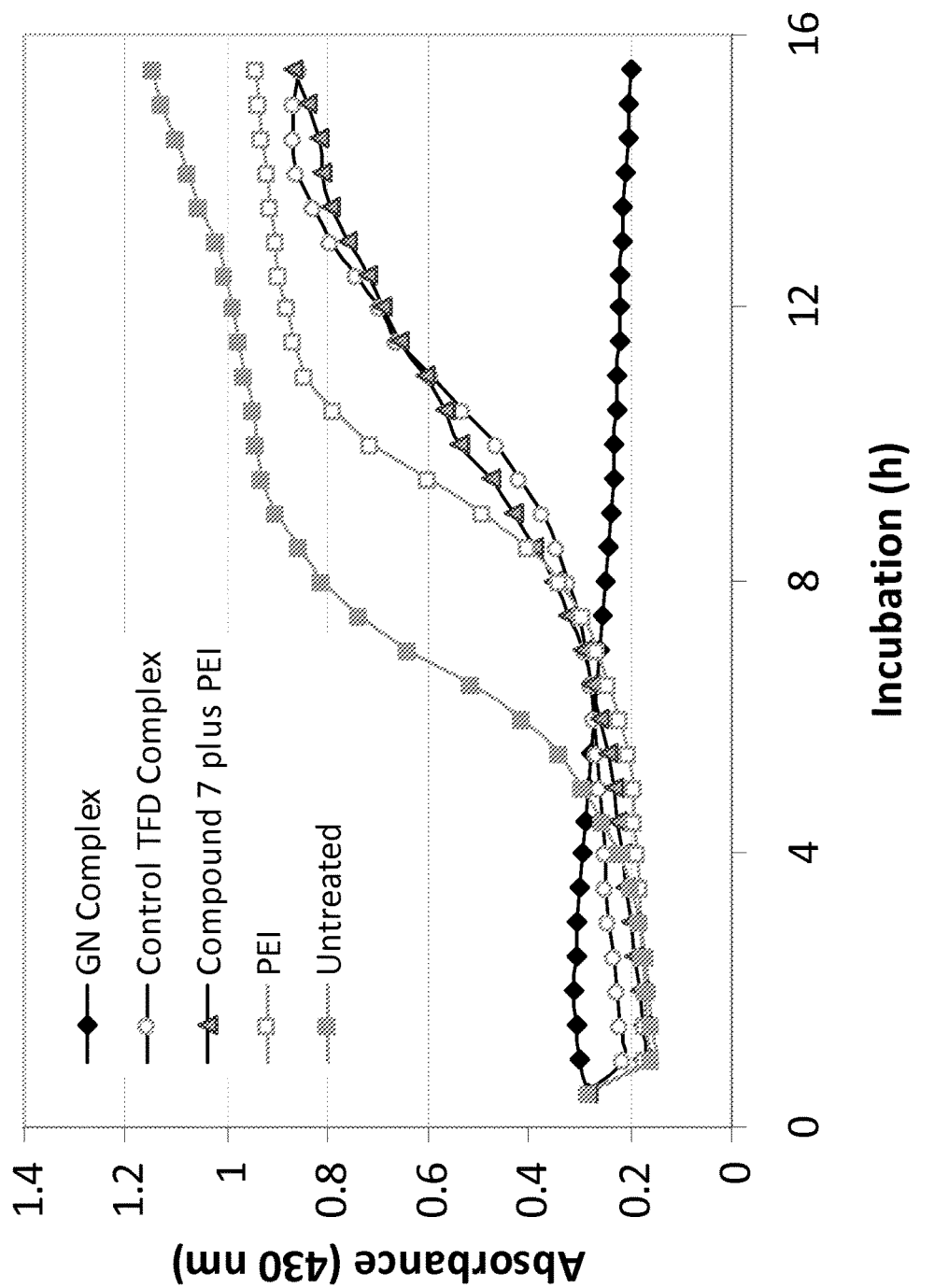

FIG. 8. In vitro bioassays demonstrating growth retardation of *E. coli* with GN_Sig TFD complexes formed with Compound 7, in the presence of PEI.

BRIEF DESCRIPTION OF THE SEQUENCES

SEQ ID NO:1—EC_Sig TFD sequence
SEQ ID NO:2—EC_Sig TFD consensus sequence
SEQ ID NO:3 & 4—EC_Sig TFD dumbbell sequences
SEQ ID NO:5 & 6—forward and reverse phosphorylated primer sequences for scrambled *E. coli* Sig binding site
SEQ ID NO:7—PA_Sig TFD sequence
SEQ ID NO:8—PA_Sig TFD consensus sequence
SEQ ID NO:9 & 10—PA_Sig TFD dumbbell sequences
SEQ ID NO:11 & 12—forward and reverse phosphorylated primer sequences for scrambled *P. aeruginosa* Sig binding site
SEQ ID NO:13 KP_Sig TFD sequence
SEQ ID NO:14—KP_Sig TFD consensus sequence
SEQ ID NO:15 & 16—KP_Sig TFD dumbbell sequences
SEQ ID NO:17 & 18—forward and reverse phosphorylated primer sequences for scrambled *K. pneumoniae* Sig binding site
SEQ ID NO:19—antimicrobial peptide sequence
SEQ ID NO:20—Gram negative Sig TFD consensus sequence SEQ ID NO:21 & 22—Gram negative Sig TFD dumbbell sequences

EXAMPLES

Although in general many of the techniques mentioned herein are well known in the art, reference may be made in particular to Sambrook and Russell, 3$^{rd}$ Edition 2001, Molecular Cloning: a laboratory manual.

Example 1

EC Sig TFD Kills *E. coli* In Vitro

A TFD containing the binding site for a sigN alternative sigma factor ($\sigma^{54}$-like) had the sequence set out in SEQ ID NO:1. The sequence was based on the promoter region of the *E. coli* glnA gene described in Barrios et al. [1999] *Nucl. Acids Res.* 22: 4305-4313:

```
EC_Sig:
                                     (SEQ ID NO: 1)
TGG CAC AGA TTT TGC T
```

Similar binding sites found in other *E. coli* genes (fdhF, hycA, hypA, nac, glnH and pspA) listed in Barrios et al were used to generate a consensus sequence using the IUPAC degenerate DNA alphabet for the binding site in *E. coli*:

```
EC_Sig Consensus:
                                     (SEQ ID NO: 2)
TGG CAC NNW WNT TGC W
```

The IUPAC single letter code is used, where: W is A or T.

The sequence of SEQ ID 1 was incorporated into a TFD and tested to see whether, when delivered to an *E. coli* culture, it would prevent growth.

Materials and Methods

Preparation of TFD Dumbbells by Ligation (DB-TFD)

Two 5'-phopshorylated oligonucleotides were synthesised, each containing one strand of the recognition site for the *E. coli* sigN protein. At either end of the molecule a small hairpin loop acted to protect the molecule from degradation. Each oligonucleotide was re-suspended in dH$_2$O at a concentration of 250 pmol/μl.

To form the *E. coli* Sig dumbbell TFD (referred to as EC_Sig TFD) the following phosphorylated oligonucleotides were synthesised:

```
EC_Sig DB1:
                                     (SEQ ID NO: 3)
CTT GGT TTT TCC AAG TGG CAC AGA TTT TGC T

EC_Sig DB2:
                                     (SEQ ID NO: 4)
CCC TCT TTT TGA GGG AGC AAA ATC TGT GCC A
```

Typically 30 μl of each oligonucleotide was mixed with 27 μl of dH$_2$O and annealed using the following PCR programme: 95° C. 3 min, cool at −0.1° C./s to 8° C., end. Following this, 10 μl of 10×NEB Ligase buffer and 3 μl HC T4 DNA ligase (NEB) were added. The mixture was incubated overnight at 16° C. The material was then extensively digested with T7 exonuclease (NEB) to remove any unligated oligonucleotides and recovered by two rounds of ethanol precipitation.

A DB TFD was also prepared containing a scrambled version of the EC_Sig binding site, referred to as EC_Scr TFD. In this instance the phosphorylated primers used were:

```
EC_Scr DB1:
                                     (SEQ ID NO: 5)
CTT GGT TTT TCC AAG ACC TAG TTA GGG TTT C

EC_Scr DB2:
                                     (SEQ ID NO: 6)
CCC TCT TTT TGA GGG GAA ACC CTA ACT AGG T
```

Preparation of Lipophilic Cation.

15 mg of Compound 7 (Sygnature Ltd; referred to as C7) was dissolved in 10 ml methanol, dried to completion using a rotary evaporator and re-suspended in 5 mM Hepes pH7.4 to a final concentration of 10 mM. Compound 7 dissolved readily to give a clear, light yellow solution which was then subjected to probe sonication on ice using an MSE Soniprep 150. The conditions used were: 60 cycles of 30 s on (amplitude 10 microns) and 60 s off. Following this treatment, the sample was entirely clear. The sample was then centrifuged to remove debris and is referred to as sC7 (sonicated Compound 7). This step formed vesicles or 'bolasomes'.

Formation of TFD Complexes

For delivery, TFDs complexes were formed with sC7. The minimum amount of C7 bolasome needed to bind 2 μg of either TFD was established empirically and the appropriate amount of bolasome mixed with TFDs in 5 mM Hepes, pH7.4, to form the complexes. Dilutions of the TFD complex were used in subsequent bioassays.

Performing Growth Studies in 96-Well Plates

A growth assay was performed using a TFD complex consisting of either the EC_Sig TFD or EC_Scr TFD to determine the effect on growth of *E. coli*. The assays to determine the effect on growth of bacterial cells were performed using 96 well plates, each well containing 200 μl of broth consisting of LB media (Luria-Bertani LB media (1% [w/v] Bacto-tryptone, 0.5% [w/v] Yeast extract, 1% [w/v] NaCl)). 1 μl of various concentrations of TFD complexes was added to each well and the effect on bacterial growth of *E. coli* was monitored by measuring absorbance of the broth at intervals during incubation. The plates were incubated at 37° C. with shaking and absorbance readings (at 450 nM) were taken using a plate reader.

Results

TFD Complexes can Efficiently Kill *E. Coli* In Vitro

*E. coli* cells were used to inoculate LB broth to give a final concentration of cells of 5×10$^5$/ml. 200 μl aliquots were dispensed into wells in a 96 well plate. Wells were supplemented with varying concentrations of EC_Sig TFD complexes, EC_Scr TFD complexes (TFD Control) or the wells were untreated. Both TFD complexes contained C7 at a concentration of 500 ng/ml and TFDs at 5 μg/ml.

As shown in FIG. 1, cell growth was essentially similar for the untreated sample and the TFD Control sample. However, the EC_Sig TFD complex prevented bacterial growth. Hence, the combination of the C7 bolasome specifically with the EC_Sig TFD killed the *E. coli* strain, whereas the control TFD complex did not. This effect was due to the complexes effectively delivering the TFD therapeutic to the bacteria. The action of delivery alone, with concomitant membrane damage, did not kill the cells because the TFD Control sample did not affect cell growth.

Example 2

PA_SIG TFD Kills *P. Aeruginosa* In Vitro

A TFD containing the binding site for a sigN alternative sigma factor ($\sigma^{54}$-like) had the sequence set out in SEQ ID NO:7. The sequence was based on the promoter region of the *P. aeruginosa* algC gene described in Barrios et al. (supra):

```
PA_Sig:
                                      (SEQ ID NO: 7)
CGG GCA ACG CAC TGC C
```

Similar binding sites found in other *P. aeruginosa* genes (oprE, cpg2, rhlAB, algD and fleSR) listed in Barrios et al were used to define a consensus sequence using the IUPAC degenerate DNA alphabet for the binding site in *P. aeruginosa*:

```
PA_Sig Consensus:
                                      (SEQ ID NO: 8)
GGN ANW CSC NTN SCN
```

The sequence of SEQ ID NO:7 was incorporated into a TFD and tested to see whether, when delivered to an *P. aeruginosa* culture, it would prevent bacterial growth.

The TFD complex was combined with an antimicrobial peptide to enable delivery of the TFD to *P. aeruginosa* cells. In this example, Buforin II was used (Park et al. [2000] *Proc. Natl. Acad. Sci. USA* 97: 8245-8250) and typically 200 µl of broth was supplemented with 1 µg of peptide.

Materials and Methods

Preparation of TFD Dumbbells by Ligation (DB-TFD)

Two 5'-phopshorylated oligonucleotides were synthesised, each containing one strand of the recognition site for the *P. aeruginosa* alternative sigma protein and ligated together to form a dumbbell TFD as described in Example 1. The sequences used were:

```
PA_Sig DB1:
                                      (SEQ ID NO: 9)
CTT GGT TTT TCC AAG CGG GCA ACG CAC TGC C

PA_Sig DB2:
                                      (SEQ ID NO: 10)
CCC TCT TTT TGA GGG GGC AGT GCG TTG CCC G
```

Similarly a scrambled version of the TFD was made using the phosphorylated primers:

```
PA_Scr DB1:
                                      (SEQ ID NO: 11)
CTT GGT TTT TCC AAG TCA AGA GGG CCC CCC

PA_Scr DB2:
                                      (SEQ ID NO: 12)
CCC TCT TTT TGA GGG GGG GGG CCC TCT TGA.
```

Growth Assays

TFD complexes were formed as described in Example 1. A growth assay was performed using a complex consisting of either the PA_Sig TFD or PA_Scr TFD to determine the effect on growth of *P. aeruginosa*. The assays to determine the effect on growth of bacterial cells were performed using 96 well plates, each well containing 200 µl of broth consisting of LB media supplemented with 1 µg/ml Buforin II.

1 µl of various concentrations of TFD complexes was added to each well and the effect on bacterial growth of *P. aeruginosa* was monitored by measuring absorbance of the broth at intervals during incubation. The plates were incubated at 37° C. with shaking and absorbance readings (at 450 nM) were taken using a plate reader.

Results

TFD Complexes can Efficiently Kill *P. Aeruginosa* In Vitro

*P. aeruginosa* cells were used to inoculate LB broth to give a final concentration of cells of $5\times10^5$/ml. 200 µl aliquots were dispensed into wells in a 96 well plate. Wells were supplemented with varying concentrations of PA_Sig TFD complexes, PA_Scr TFD complexes (TFD Control), a Delivery Control consisting of Compound 7 added to the Buforin (to test for synergy) or the wells were untreated. Both TFD complexes contained C7 at a concentration of 500 ng/ml and TFDs at 5 µg/ml.

As shown in FIG. 2, cell growth was essentially similar for the untreated sample, the Delivery Control and the TFD Control sample. However, the PA_Sig TFD Complex prevented bacterial growth. Hence, the combination of the delivery vehicle specifically with the PA_Sig TFD killed the *P. aeruginosa* strain, whereas the control TFD complex did not. This effect was due to the complexes effectively delivering the TFD therapeutic to the bacteria. The action of delivery alone, with concomitant membrane damage, did not kill the cells as the TFD Control sample did not affect cell growth.

Example 3

KP_SIG TFD Kills *K. Pneumoniae* In Vitro

A TFD containing the binding site for a sigN alternative sigma factor ($\sigma^{54}$-like) has the sequence set out in SEQ ID NO:13. The sequence is based on the promoter region of the *K. pneumoniae* glnA gene described in Barrios et al. (supra):

```
KP_Sig:
                                      (SEQ ID NO: 13)
TGG CAC AGA TTT CGC T
```

Similar binding sites found in other *K. pneumoniae* genes (nifB, nifE, nifH, nifJ, nifL, nifM and nifU) listed in Barrios et al were used to generate a consensus sequence using the IUPAC degenerate DNA alphabet for the binding site in *K. pneumoniae*:

```
KP_Sig Consensus:
                                      SEQ ID NO: 14)
TGG NNN NNN WTT TGC W
```

The sequence of SEQ ID NO:13 was incorporated into a TFD and tested to see whether, when delivered to an *K. pneumoniae* culture, it would prevent growth.

Preparation of TFD Dumbbells by Ligation (DB-TFD)

Two 5'-phopshorylated oligonucleotides were synthesised, each containing one strand of the recognition site for the *K. pneumoniae* alternative sigma protein and ligated together to form a dumbbell TFD as described in Example 1. The sequences used were:

```
KP_Sig DB1:
                                 (SEQ ID NO: 15)
CTT GGT TTT TCC AAG TGG CAC AGA TTT CGC T

KP_Sig DB2:
                                 (SEQ ID NO: 16)
CCC TCT TTT TGA GGG AGC GAA ATC TGT GCC A
```

Similarly, a scrambled version of the TFD was made using the phosphorylated primers:

```
KP_Scr DB1:
                                 (SEQ ID NO: 17)
CTT GGT TTT TCC AAG CTA CAT TTA GCG GTG C

KP_Scr DB2:
                                 (SEQ ID NO: 18)
CCC TCT TTT TGA GGG GCA CCG CTA AAT GTA G
```

The TFD complex was combined with an antimicrobial peptide to enable delivery to *K. pneumoniae* cells. Transfection was achieved by complexing the TFD with a cell penetrating peptide. The peptide has been previously described and found to be capable of penetrating the membrane of *K. pneumoniae* (Vaara [1996] *Antimicrob. Agents Chemother.* 40: 1801). The sequence of the peptide used was:

```
KP Transfection peptide:
                                 (SEQ ID NO: 19)
IKFLKFLKFL
```

Growth Assays

TFD complexes were formed as described in Example 1. A growth assay was performed using a complex consisting of either the KP_Sig TFD or KP_Scr TFD to determine their effect on growth of *K. pneumoniae*. The assays to determine the effect on growth of bacterial cells were performed using 96 well plates, each well containing 200 µl of broth consisting of M9 media supplemented with 5 µg/ml IKFLKFLKFL peptide. 1 µl of various concentrations of TFD complexes was added to each well and the effect on bacterial growth of *K. pneumoniae* was monitored by measuring absorbance of the broth at intervals during incubation. The plates were incubated at 37° C. with shaking and absorbance readings (at 450 nM) were taken using a plate reader.

Results

TFD Complexes can Efficiently Kill *K. Pneumoniae* In Vitro

*K. pneumoniae* cells were used to inoculate M9 broth supplemented with 1 µg/ml IKFLKFLKFL peptide to give a final concentration of cells of $5 \times 10^5$/ml. 200 µl aliquots were dispensed into wells in a 96 well plate. Wells were supplemented with varying concentrations of KP_Sig TFD complexes, EC_Scr TFD complexes (TFD Control) or the wells were untreated. Both TFD complexes contained C7 at a concentration of 500 ng/ml and TFDs at 5 µg/ml.

As shown in FIG. 3, cell growth was essentially similar for the untreated sample and the TFD Control sample. However, the KP_Sig TFD Complex prevented bacterial growth. Hence, the combination of the C7 bolasome specifically with the KP_Sig TFD killed the *K. pneumoniae* strain, whereas the control TFD complex did not. This effect was due to the complexes effectively delivering the TFD therapeutic to the bacteria. The action of delivery alone, with concomitant membrane damage, did not kill the cells as the TFD Control sample did not affect cell growth.

Example 4

Consensus SIG TFD Kills Both *E. Coli* and *P. Aeruginosa* In Vitro

By visual examination of the above consensus sequences (SEQ ID NO:2, SEQ ID NO:8 and SEQ ID NO:14) a Gram-Negative consensus sequence was derived:

```
GNeg Consensus:
                                 (SEQ ID NO: 20)
TGG CAC ACA TAT TGC A
```

Experiments were carried out to test the prediction that a TFD with this consensus sequence will function as a Sig TFD in *E. coli*, *P. aeruginosa* and *K. pneumoniae*, as well as other Gram-negative infections.

Materials and Methods

Preparation of TFD Dumbbells by Ligation (DB-TFD)

Two 5'-phopshorylated oligonucleotides were synthesised, each containing one strand of the recognition site for Gram-negative alternative sigma proteins and ligated together to form a dumbbell TFD as described in Example 1. The sequences used were:

```
GN_Sig DB1:
                                 (SEQ ID NO: 21)
CTT GGT TTT TCC AAG TGG CAC ACA TAT TGC A

GN_Sig DB2:
                                 (SEQ ID NO: 22)
CCC TCT TTT TGA GGG TGC AAT ATG TGT GCC A
```

Growth Assays

TFD complexes were formed as described in Example 2. A growth assay was performed using a complex consisting of either the GN_Sig TFD or PA_Scr TFD (Example 2; SEQ ID NOS:11 and 12) to determine the effect on growth of a mixed culture of *E. coli* and *P. aeruginosa*. The assays to determine the effect on growth of bacterial cells were performed using 96 well plates, each well containing 200 µl of broth consisting of LB media supplemented with 1 µg/ml Buforin II. 1 µl of TFD complexes or controls was added to each well, as well as 1 in 2 and 1 in 10 dilutions. The effect on bacterial growth of both species was assessed by incubating the plates overnight at 37° C. with shaking.

Results

GN TFD complexes can efficiently kill both *E. coli* and *P. aeruginosa* in vitro Only cells treated with all dilutions of the GN TFD complex and Buforin II failed to grow in this assay (FIG. 5). Bacteria in all other conditions grew: untreated cells, cells treated with similar concentration of a Control TFD complex with Buforin II, and a control with similar concentrations of the delivery compounds, Buforin II and Compound 7. Hence, delivery of a consensus TFD can simultaneously kill two Gram-negative pathogens.

Example 5

Consensus SIG TFD Kills Both *E. Coli* In Vitro

By visual examination of the above consensus sequences (SEQ ID NO:2, SEQ ID NO:8 and SEQ ID NO:14) a Gram-Negative consensus sequence was derived:

```
GNeg Consensus:
                                          (SEQ ID NO: 20)
        TGG CAC ACA TAT GC A
```

Experiments were carried out to test the prediction that a TFD with this consensus sequence will function as a Sig TFD in E. coli, P. aeruginosa and K. pneumoniae, as well as other Gram-negative infections.

Materials and Methods

Preparation of TFD Dumbbells by Ligation (DB-TFD)

Two 5'-phopshorylated oligonucleotides were synthesised, each containing one strand of the recognition site for Gram-negative alternative sigma proteins and ligated together to form a dumbbell TFD as described in Example 1. The sequences used were:

```
GN_Sig DB1:
                                          (SEQ ID NO: 21)
        CTT GGT TTT TCC AAG TGG CAC ACA TAT GC A

GN_Sig DB2:
                                          (SEQ ID NO: 22)
        CCC TCT TTT TGA GGG TGC AAT ATG TGT GCC A
```

Growth Assays

TFD complexes were formed as described in Example 2. A growth assay was performed using a complex consisting of either the GN_Sig TFD or PA_Scr TFD (Example 2; SEQ ID NOS:11 and 12) to determine the effect on growth of a culture of P. aeruginosa. The assays to determine the effect on growth of bacterial cells were performed using 96 well plates, each well containing 200 µl of broth consisting of LB media supplemented with 8 µg/ml polyethyleneimine (PEI). This polycationic polymer has been previously shown to permeabilise Gram-negative bacteria and render them more sensitive to antibiotics by disrupting the outer membrane of these bacteria (Helander et al. [1997] Microbiology 143: 3193-3199). 1 µl of TFD complexes or controls was added to each well, as well as 1 in 2 and 1 in 10 dilutions. The effect on bacterial growth of both species was assessed by incubating the plates overnight at 37° C. with shaking.

Results

GN TFD Complexes can Efficiently Kill E. Coli In Vitro

Only cells treated with all dilutions of the GN TFD complex and PEI failed to grow in this assay (FIG. 8). Bacteria in all other conditions grew: untreated cells, cells treated with similar concentration of a Control TFD complex with PEI, and a control with similar concentrations of the delivery compounds, PEI and Compound 7. Hence, delivery of a consensus TFD, mediated by PEI, can kill E. coli species. PEI has several advantages over the use of Buforin II, or other antimicrobial peptides: it is a low cost commodity product and is considered non-toxic (Helander et al. [1998] Microbiology 144: 385-390) and therefore may be considered a suitable excipient in formulation of TFDs.

---

The invention claimed is:

1. An antibacterial complex comprising:
   i) a decoy nucleic acid sequence comprising a sequence comprising or encoding a binding site for bacterial sigN alternative sigma54 factor, wherein the sequence comprising or encoding the binding site for bacterial sigN alternative sigma54 factor is selected from the group consisting of SEQ ID NO:2, SEQ ID NO:8, SEQ ID NO:14, SEQ ID NO:20, SEQ ID NOS:3 and 4, SEQ ID NOS:9 and 10, SEQ ID NOS:15 and 16, SEQ ID NO:21, and SEQ ID NO:22; and
   ii) one or more delivery moieties represented by the formula:

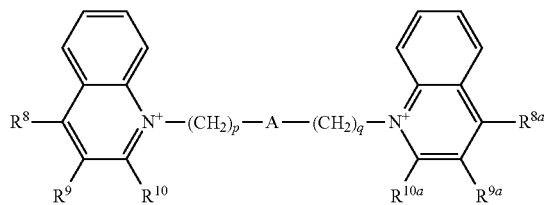

wherein:
   A is a bond;
   p and q are the same or different and each is an integer from 1 to 12; provided that the sum of p and q is in the range from 6 to 18;
   $R^8$ and $R^{8a}$ are each selected from hydrogen; $C_{1-4}$ alkoxy; nitro; amino; mono- and di-$C_{1-4}$ alkylamino; and guanidinyl;
   $R^9$ is hydrogen;
   $R^{9a}$ is hydrogen;
   $R^{10}$ is selected from hydrogen; amino; and $C_{1-4}$ alkyl optionally substituted with one or more fluorine atoms;
   $R^{10a}$ is selected from hydrogen; amino; and $C_{1-4}$ alkyl optionally substituted with one or more fluorine atoms;
   or $R^9$ and $R^{10}$ link together to form an alkylene chain $(CH_2)_w$ wherein w is 3 to 5: and/or
   $R^{9a}$ and $R^{10a}$ link together to form an alkylene chain $(CH_2)_w$ wherein w is 3 to 5 provided that the compound of the formula is other than dequalinium,
   wherein the decoy nucleic acid sequence is complexed with the one or more delivery moieties.

2. The antibacterial complex of claim 1, wherein the alkyl chain has 12 or 14 methyl groups.

3. The antibacterial complex of claim 2, wherein the delivery moiety has the formula:

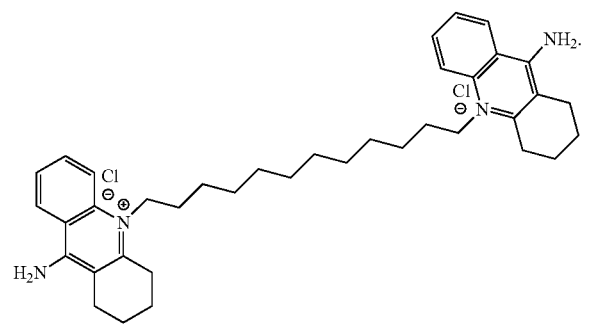

4. A method of killing bacteria or inhibiting bacterial growth, the method comprising administering to a subject an antibacterial complex comprising:

i) a decoy nucleic acid comprising a sequence comprising or encoding a binding site for bacterial sigN alternative sigma54 factor, wherein the sequence comprising or encoding the binding site for bacterial sigN alternative sigma54 factor is selected from the group consisting of SEQ ID NO:2, SEQ ID NO:8, SEQ ID NO:14, SEQ ID NO:20, SEQ ID NOS:3 and 4, SEQ ID NOS:9 and 10, SEQ ID NOS:15 and 16, SEQ ID NO:21 and SEQ ID NO:22; and
   ii) one or more delivery moieties represented by the formula:

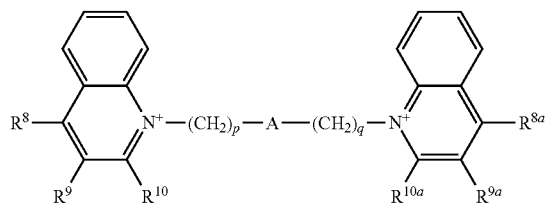

wherein:
   A is a bond;
   p and q are the same or different and each is an integer from 1 to 12; provided that the sum of p and q is in the range from 6 to 18;
   $R^8$ and $R^{8a}$ are each selected from hydrogen; $C_{1-4}$ alkoxy; nitro; amino; mono- and di-$C_{1-4}$ alkylamino; and guanidinyl;
   $R^9$ is hydrogen;
   $R^{9a}$ is hydrogen;
   $R^{10}$ is selected from hydrogen; amino; and $C_{1-4}$ alkyl optionally substituted with one or more fluorine atoms;
   $R^{10a}$ is selected from hydrogen; amino; and $C_{1-4}$ alkyl optionally substituted with one or more fluorine atoms;
   or $R^9$ and $R^{10}$ link together to form an alkylene chain $(CH_2)_w$ wherein w is 3 to 5; and/or
   $R^{9a}$ and $R^{10a}$ link together to form an alkylene chain $(CH_2)_w$ wherein w is 3 to 5 provided that the compound of the formula is other than dequalinium,
   wherein the decoy nucleic acid sequence is complexed with the one or more delivery moieties.

5. The method of claim 4, wherein the alkyl chain has 12 or 14 methyl groups.

6. A disinfectant composition comprising the antibacterial complex of claim 1 in combination with a solvent, wherein the solvent is an aqueous or organic solvent or a combination thereof.

7. The disinfectant composition of claim 6, wherein the alkyl chain has 12 or 14 methyl groups.

8. The disinfectant composition of claim 6, wherein the delivery moiety has the formula:

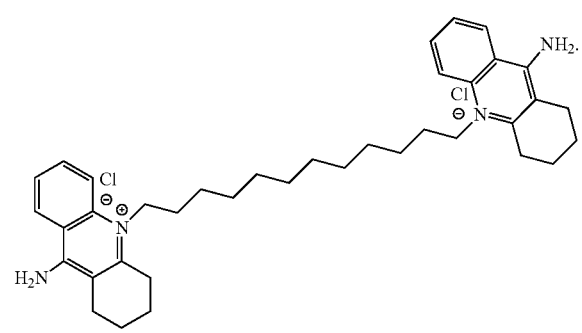

9. The antibacterial complex according to claim 1, wherein the sequence comprising or encoding the binding site for bacterial sign alternative sigma54 factor is selected from the group consisting of SEQ ID NOs:3 and 4, SEQ ID NOs:9 and 10, SEQ ID NOs:15 and 16 and SEQ ID NOs:21 and 22.

10. An antibacterial complex comprising a decoy nucleic acid sequence comprising or encoding a binding site for bacterial sigN alternative sigma54 factor, wherein the sequence comprising or encoding the binding site for bacterial sigN alternative sigma54 factor is selected from the group consisting of SEQ ID NO:2, SEQ ID NO:8, SEQ ID NO:14 and SEQ ID NO:20, and one or more delivery moieties represented by the formula:

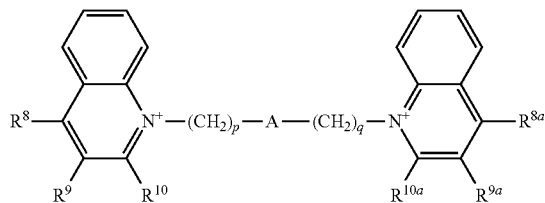

wherein:
A is a bond;
p and q are the same or different and each is an integer from 1 to 12; provided that the sum of p and q is in the range from 6 to 18;
$R^8$ and $R^{8a}$ are each selected from hydrogen; $C_{1-4}$ alkoxy; nitro; amino; mono- and di-$C_{1-4}$ alkylamino; and guanidinyl;
$R^9$ is hydrogen;
$R^{9a}$ is hydrogen;
$R^{10}$ is selected from hydrogen; amino; and $C_{1-4}$ alkyl optionally substituted with one or more fluorine atoms;
$R^{10a}$ is selected from hydrogen; amino; and $C_{1-4}$ alkyl optionally substituted with one or more fluorine atoms;
or $R^9$ and $R^{10}$ link together to form an alkylene chain $(CH_2)_w$ wherein w is 3 to 5; and/or
$R^{9a}$ and $R^{10a}$ link together to form an alkylene chain $(CH_2)_w$ wherein w is 3 to 5 provided that the compound of the formula is other than dequalinium,
wherein the decoy nucleic acid sequence is complexed with the one or more delivery moieties.

11. The antibacterial complex as claimed in claim 10, wherein the alkyl chain has 12 or 14 methyl groups.

12. The antibacterial complex as claimed in claim 10, wherein the delivery moiety has the formula:

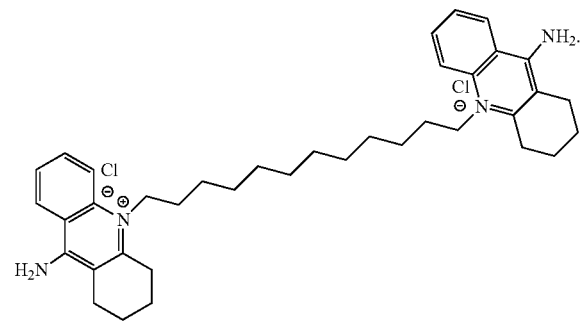

13. A method of treating a bacterial infection comprising administering the antibacterial complex as claimed in claim 1 to an individual in need thereof.

14. The method as claimed in claim 13, wherein the treatment of bacterial infection additionally comprises administering one or more antibiotics and/or other antibacterial agent(s).

15. A pharmaceutical composition or medicament comprising the antibacterial complex of claim 1, and a physiologically acceptable carrier or excipient.

16. A pharmaceutical composition or medicament comprising an antibacterial complex as claimed in claim 10, and a physiologically acceptable carrier or excipient.

17. A method of treating bacterial infection comprising administering the antibacterial complex as claimed in claim 10 to an individual in need thereof.

18. The method of claim 13, wherein treating bacterial infection comprises treating a condition selected from the group consisting of: pneumonia, bacteraemia, whooping cough, Lyme's disease, brucellosis, acute enteritis, septicaemia, tularaemia, influenza, peptic ulcers, Legionnaire's disease, gonorrhoea, noscomial infections, sepsis, ricketts, typhoid, dysentery, cholera, plague, anthrax, pseudomembranous colitis, diphtheria, listerosis, tuberculosis, septicaemia, Q-fever and meningitis.

19. The method of claim 17, wherein treating bacterial infection comprises treating a condition selected from the group consisting of pneumonia, bacteraemia, whooping cough, Lyme's disease, brucellosis, acute enteritis, septicaemia, tularaemia, influenza, peptic ulcers, Legionnaire's disease, gonorrhoea, noscomial infections, sepsis, ricketts, typhoid, dysentery, cholera, plague, anthrax, pseudomembranous colitis, diphtheria, listerosis, tuberculosis, septicaemia, Q-fever and meningitis.

20. An ex vivo method of killing bacteria, inhibiting bacterial growth, or reducing bacterial virulence, the method comprising applying the disinfectant composition according to claim 6.

21. A disinfectant composition according to claim 6 in combination with one or more antibiotics and/or antibacterial agents.

22. An ex vivo method of killing bacteria, inhibiting bacterial growth, or reducing bacterial virulence, the method comprising applying the disinfectant composition according to claim 21.

23. A disinfectant composition comprising an antibacterial complex as claimed in claim 10 in combination with one or more antibiotics.

24. A kit comprising the antibacterial complex of claim 1, and one or more antibiotics and/or antibacterial agents, wherein the antibacterial complex and the one or more antibiotics and/or antibacterial agents are for combined use in killing bacteria, inhibiting bacterial growth, or reducing bacterial virulence.

25. A kit comprising the antibacterial complex as claimed in claim 10, and one or more antibiotics, wherein the antibacterial complex and the one or more antibiotics are for combined use in killing bacteria, inhibiting bacterial growth, or reducing bacterial virulence.

26. The pharmaceutical composition or medicament as claimed in claim 15 in combination with one or more antibiotics.

27. A pharmaceutical composition or medicament as claimed in claim 16 in combination with one or more antibiotics and/or antibacterial agents.

28. An antibacterial complex according to claim 1 wherein $R^{10}$ is selected from hydrogen; amino; and $C_{1-4}$ alkyl optionally substituted with one or more fluorine atoms; and $R^{10a}$ is selected from hydrogen; amino; and $C_{1-4}$ alkyl substituted with one or more fluorine atoms;

or $R^9$ and $R^{10}$ link together to form an alkylene chain $(CH_2)_w$ wherein w is 3 to 5: and/or $R^{9a}$ and $R^{10a}$ link together to form an alkylene chain $(CH_2)_w$ wherein w is 3 to 5.

29. A complex according to claim 1 wherein $R^9$ and $R^{10}$ link together to form an alkylene chain $(CH_2)_w$ wherein w is 3 to 5: and/or $R^{9a}$ and $R^{10a}$ link together to form an alkylene chain $(CH_2)_w$ wherein w is 3 to 5.

30. A complex according to claim 29, wherein $R^9$ and $R^{10}$ link together to form an alkylene chain $(CH_2)_w$ wherein w is 3 to 5: and $R^{9a}$ and $R^{10a}$ link together to form an alkylene chain $(CH_2)_w$ wherein w is 3 to 5.

31. The disinfectant composition according to claim 6 wherein $R^{10}$ is selected from hydrogen; amino; and $C_{1-4}$ alkyl optionally substituted with one or more fluorine atoms; and $R^{10a}$ is selected from hydrogen; amino; and $C_{1-4}$ alkyl substituted with one or more fluorine atoms;

or $R^9$ and $R^{10}$ link together to form an alkylene chain $(CH_2)_w$ wherein w is 3 to 5: and/or $R^{9a}$ and $R^{10a}$ link together to form an alkylene chain $(CH_2)_w$ wherein w is 3 to 5.

32. The disinfectant composition according to claim 6 wherein $R^9$ and $R^{10}$ link together to form an alkylene chain $(CH_2)_w$ wherein w is 3 to 5: and/or $R^{9a}$ and $R^{10a}$ link together to form an alkylene chain $(CH_2)_w$ wherein w is 3 to 5.

33. The disinfectant composition according to claim 32, wherein $R^9$ and $R^{10}$ link together to form an alkylene chain $(CH_2)_w$ wherein w is 3 to 5: and $R^{9a}$ and $R^{10a}$ link together to form an alkylene chain $(CH_2)_w$ wherein w is 3 to 5.

34. An antibacterial complex according to claim 10 wherein $R^{10}$ is selected from hydrogen; amino; and $C_{1-4}$ alkyl optionally substituted with one or more fluorine atoms; and $R^{10a}$ is selected from hydrogen; amino; and $C_{1-4}$ alkyl substituted with one or more fluorine atoms;

or $R^9$ and $R^{10}$ link together to form an alkylene chain $(CH_2)_w$ wherein w is 3 to 5: and/or $R^{9a}$ and $R^{10a}$ link together to form an alkylene chain $(CH_2)_w$ wherein w is 3 to 5.

35. A complex according to claim 10 wherein $R^9$ and $R^{10}$ link together to form an alkylene chain $(CH_2)_w$ wherein w is 3 to 5: and/or $R^{9a}$ and $R^{10a}$ link together to form an alkylene chain $(CH_2)_w$ wherein w is 3 to 5.

36. A complex according to claim 35, wherein $R^9$ and $R^{10}$ link together to form an alkylene chain $(CH_2)_w$ wherein w is 3 to 5: and $R^{9a}$ and $R^{10a}$ link together to form an alkylene chain $(CH_2)_w$ wherein w is 3 to 5.

37. The method as claimed in claim 17, wherein the treatment of bacterial infection additionally comprises administering one or more antibiotics and/or other antibacterial agent(s).

* * * * *

UNITED STATES PATENT AND TRADEMARK OFFICE
CERTIFICATE OF CORRECTION

PATENT NO. : 9,550,991 B2
APPLICATION NO. : 13/638764
DATED : January 24, 2017
INVENTOR(S) : Michael McArthur It is certified that error appears in the above-identified patent and that said Letters Patent is hereby corrected as shown below:

On the Title Page

In Column 2 (page 2, item (56)) at Line 31, Under Other Publications, change "faecilis" to --faecalis--.

In Column 2 (page 2, item (56)) at Line 63, Under Other Publications, change "Permagon," to --Pergamon,--.

In the Specification

In Column 1 at Line 39, Change "baumanii" to --baumannii--.

In Column 1 at Line 65, Change "baumanni" to --baumannii--.

In Column 2 at Line 11, Change "baumanni" to --baumannii--.

In Column 2 at Line 25, Change "Microbio." to --Microbiol.--.

In Column 3 at Line 4, Change "al" to --al.--.

In Column 4 at Line 38, Change "Heliobacter" to --Helicobacter--.

In Column 4 at Line 65, Change "NOs 21" to --NOs:21--.

In Column 5 at Line 30, Change "bacteristatic" to --bacteriostatic--.

In Column 5 at Line 41, Change "(cephaloradine)," to --(cephaloridine),--.

In Column 5 at Line 42, Change "Cefadryl)," to --Cefadyl),--.

Signed and Sealed this
Thirteenth Day of June, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,550,991 B2

In Column 5 at Line 48, Change "Cefinetazole," to --Cefmetazole,--.

In Column 5 at Lines 49-50, Change "cefbuperazone, cefinetazole" to --cefoperazone, cefmetazole--.

In Column 5 at Line 54, Change "Cefinenoxime," to --Cefmenoxime,--.

In Column 5 at Line 62, After "flomoef" insert --;--.

In Column 5 at Line 65, Change "Cefinepidium," to --Cefmepidium,--.

In Column 5 at Line 67, After "Cefuracetime" insert --.--.

In Column 6 at Line 32, After "variants" insert --.--.

In Column 6 at Line 33, Change "Streptoaramins:" to --Streptogramins:--.

In Column 7 at Line 53, Change "NOs 21" to --NOs:21--.

In Column 8 at Line 36 (approx.), Change "(CH=CH)$_1$—;" to --(CH=CH)$_t$—;--.

In Column 10 at Line 11 (approx.), Change "(Guiterrez-Lugo" to --(Gutierrez-Lugo--.

In Column 10 at Line 16 (approx.), Change "paxcitol," to --paxcutol,--.

In Column 11 at Line 5, Change "(CH=CH)$_1$—;" to --(CH=CH)$_t$—;--.

In Column 13 at Line 34, Change "(CH$_2$)," to --(CH$_2$)$_w$--.

In Column 14 at Line 11 (approx.), Change "al" to --al.--.

In Column 15 at Line 7, Change "], diiodide" to --]diiodide--.

In Column 15 at Line 9, Change "], diiodide" to --]diiodide--.

In Column 15 at Line 11, Change "], diiodide" to --]diiodide--.

In Column 15 at Line 13, Change "], diiodide" to --]diiodide--.

In Column 15 at Line 15, Change "], diiodide" to --]diiodide--.

In Column 16 at Line 18, Change "amino]-10-[N-" to --amino]-10-[N'- --.

In Column 16 at Line 21, Change "amino]-[2-(N" to --amino]-12-(N'--.

In Column 16 at Line 27, Change "amino]-10-[N-" to --amino]-10-[N'- --.

In Column 16 at Line 43, Change "bis(1-" to --bis(11- --.

In Column 16 at Line 52, Change "al" to --al.--.

In Column 16 at Line 53, Change "al" to --al.--.

In Column 16 at Line 56, Change "al" to --al.--.

In Column 17 at Line 25, Change "al," to --al.--.

In Column 17 at Lines 42-43, Change "20 nM, 20 nM, 40 nM" to --20 nM, 30 nM, 40 nM,--.

In Column 18 at Line 3, Change "affect" to --effect--.

In Column 18 at Line 8, Change "dequlanium," to --dequalinium,--.

In Column 19 at Line 5, Change "bacteriocidal" to --bactericidal--.

In Column 20 at Line 48 (approx.), Change "al" to --al.--.

In Column 20 at Line 53 (approx.), Change "al" to --al.--.

In Column 21 at Line 2, Change "Catioinic" to --Cationic--.

In Column 21 at Line 53, Change "quarternary" to --quaternary--.

In Column 21 at Line 62, Change "quarternary" to --quaternary--.

In Column 22 at Line 48, Change "bacteriocidal" to --bactericidal--.

In Column 23 at Line 36, After "149)" insert --.--.

In Column 23 at Line 40, Change "bucchal" to --buccal--.

In Column 25 at Line 19, Change "barumannii" to --baumannii--.

In Column 25 at Line 23, Change "burnetti" to --burnetii--.

In Column 25 at Line 27, Change "pneumophilla" to --pneumophila--.

In Column 25 at Lines 28-29, Change "menigitidis" to --meningitidis--.

In Column 25 at Line 29, Change "Acinetobacteria" to --Acinetobacter--.

In Column 25 at Line 29, Change "(Noscomia;" to --(Nosocomial;--.

In Column 25 at Line 37, Change "diptheriae (Diptheria)," to --diphtheriae (Diphtheria),--.

In Column 25 at Line 38, Change "(Noscomial" to --(Nosocomial--.

In Column 25 at Line 38, Change "Listeris" to --Listeria--.

In Column 25 at Lines 38-39, Change "(Listerosis" to --(Listeriosis--.

In Column 25 at Line 44, Change "Acientobacter," to --Acinetobacter,--.

In Column 25 at Line 45, Change "Proteobacter;" to --Proteobacteria;--.

In Column 27 at Line 27, Change "al" to --al.--.

In Column 27 at Line 36, Change "ID 1" to --ID NO:1--.

In Column 27 at Line 41, Change "5'-phopshorylated" to --5'-phosphorylated--.

In Column 29 at Line 16 (approx.), Change "al" to --al.--.

In Column 29 at Line 36, Change "5'-phopshorylated" to --5'-phosphorylated--.

In Column 30 at Line 50, Change "al" to --al.--.

In Column 30 at Line 63, Change "5'-phopshorylated" to --5'-phosphorylated--.

In Column 32 at Line 22 (approx.), Change "5'-phopshorylated" to --5'-phosphorylated--.

In Column 32 at Line 39, Change "NOS:11" to --NOs:11--.

In Column 33 at Line 11, Change "5'-phopshorylated" to --5'-phosphorylated--.

In Column 34 at Line 1, Change "NOS:11" to --NOs:11--.

In the Claims

In Column 41 at Line 9 (approx.), In Claim 1, change "NOS:3" to --NOs:3--.

In Column 41 at Line 10 (approx.), In Claim 1, change "NOS:9" to --NOs:9--.

In Column 41 at Line 10 (approx.), In Claim 1, change "NOS:15" to --NOs:15--.

In Column 42 at Line 7, In Claim 4, change "NOS:3" to --NOs:3--.

In Column 42 at Line 7, In Claim 4, change "NOS:9" to --NOs:9--.

CERTIFICATE OF CORRECTION (continued)
U.S. Pat. No. 9,550,991 B2

In Column 42 at Line 8, In Claim 4, change "NOS:15" to --NOs:15--.

In Column 42 at Line 37, In Claim 4, change "5;" to --5:--.

In Column 43 at Line 3, In Claim 9, change "sign" to --sigN--.

In Column 43 at Line 42 (approx.), In Claim 10, change "5;" to --5:--.

In Column 44 at Line 23, In Claim 18, change "noscomial" to --nosocomial--.

In Column 44 at Line 23, In Claim 18, change "ricketts," to --rickets,--.

In Column 44 at Line 25, In Claim 18, change "listerosis," to --listeriosis,--.

In Column 44 at Line 33 (approx.), In Claim 19, change "noscomial" to --nosocomial--.

In Column 44 at Line 33 (approx.), In Claim 19, change "ricketts," to --rickets,--.

In Column 44 at Line 35 (approx.), In Claim 19, change "listerosis," to --listeriosis,--.